United States Patent
Baurmeister et al.

[11] Patent Number: 6,022,478
[45] Date of Patent: Feb. 8, 2000

[54] DEVICE AND PROCESS FOR THE SUBSTANCE-SPECIFIC TREATMENT OF FLUIDS

[75] Inventors: Ulrich Baurmeister, Wuppertal; Rudolf Wollbeck, Erlenbach, both of Germany

[73] Assignee: Akzo Nobel N.V., Arnhem, Netherlands

[21] Appl. No.: 08/794,638

[22] Filed: Feb. 3, 1997

[30] Foreign Application Priority Data

Feb. 1, 1996 [DE] Germany .......................... 196 03 523

[51] Int. Cl.[7] ............................... B01D 61/00; C02F 1/00
[52] U.S. Cl. ................ 210/651; 210/321.6; 210/321.83; 210/433.1; 210/434; 210/500.23; 210/650; 210/652; 210/790
[58] Field of Search ........................... 210/321.6, 321.74, 210/321.79, 321.8, 321.83, 321.88, 321.89, 500.23, 500.36, 500.42, 502.1, 638, 642, 650, 651, 653, 660, 687, 664, 805, 416.3, 321.78, 790, 433.1, 434; 405/15, 258, 264

[56] References Cited

U.S. PATENT DOCUMENTS

| | | |
|---|---|---|
| 32,815 | 7/1861 | Arnold . |
| 472,547 | 4/1892 | Nordtmeyer . |
| 3,536,611 | 10/1970 | De Filippi et al. . |
| 4,061,141 | 12/1977 | Hydén et al. . |
| 4,163,714 | 8/1979 | Gregor . |
| 4,172,794 | 10/1979 | Sigdell . |
| 4,202,775 | 5/1980 | Abe et al. . |
| 4,266,026 | 5/1981 | Breslau . |
| 4,451,369 | 5/1984 | Sekino . |
| 4,578,191 | 3/1986 | Jaffrin et al. . |

(List continued on next page.)

FOREIGN PATENT DOCUMENTS

| | | |
|---|---|---|
| 112094-A1 | 6/1984 | European Pat. Off. . |
| 173500-A1 | 3/1986 | European Pat. Off. . |
| 280840-A1 | 9/1988 | European Pat. Off. . |
| 285812-A1 | 10/1988 | European Pat. Off. . |
| 341413-A2 | 11/1989 | European Pat. Off. . |
| 521495-A2 | 1/1993 | European Pat. Off. . |
| 565978-A1 | 10/1993 | European Pat. Off. . |
| 610755-A1 | 8/1994 | European Pat. Off. . |
| 662340-A1 | 7/1995 | European Pat. Off. . |
| 68910175-T2 | 2/1994 | Germany . |
| 19501726-A1 | 7/1996 | Germany . |
| 1432018 | 4/1976 | United Kingdom . |
| WO 80/02805 | 12/1980 | WIPO . |
| WO 90/04609 | 5/1990 | WIPO . |
| WO 90/05018 | 5/1990 | WIPO . |
| WO 93/02777 | 2/1993 | WIPO . |

OTHER PUBLICATIONS

E. Klein, *Affinity Membranes*, "Their Chemistry and Performance in Adsorptive Separation Processes", John Wiley & Sons, Inc. (1991).

(List continued on next page.)

*Primary Examiner*—John Kim
*Assistant Examiner*—Michael Fleming
*Attorney, Agent, or Firm*—Oliff & Berridge, PLC

[57] ABSTRACT

Device and process for the substance-specific treatment of fluids by means of treatment elements made from porous membranes, arranged in a casing, where the treatment elements have cavities which are closed or open in the direction of the outlet arrangement of the casing and the treatment elements are arranged in the casing such that a continuous channel system is formed around them and which substantially surrounds them. The fluid to be treated flows as the primary stream around the treatment elements along essentially their entire exterior, and part of this primary stream flows as a secondary stream through the porous membrane wall of the treatment elements wherein the substance-specific treatment is performed, collects in the cavities and leaves the treatment elements again in order to be reunited with the primary stream within the casing.

56 Claims, 9 Drawing Sheets

U.S. PATENT DOCUMENTS

| | | |
|---|---|---|
| 4,704,205 | 11/1987 | Ishii . |
| 4,741,832 | 5/1988 | Leonard . |
| 4,767,544 | 8/1988 | Hamblin . |
| 4,935,142 | 6/1990 | Sternberg . |
| 4,963,494 | 10/1990 | Hibino et al. . |
| 5,019,270 | 5/1991 | Afeyan et al. . |
| 5,066,401 | 11/1991 | Müller et al. . |
| 5,141,031 | 8/1992 | Baurmeister . |
| 5,556,708 | 9/1996 | Hörl et al. . |
| 5,683,916 | 11/1997 | Goffe et al. . |

OTHER PUBLICATIONS

S. Brandt et al., "Membrane–Based Affinity Technology for Commercial Scale Purifications", *Bio/Technology*, vol. 6 (1988), pp. 779–782.

K. Sakai, "Determination of pore size and pore size distribution. 2. Dialysis membranes", *Journal of Membrane Science*, 96 (1994), pp. 91–130.

S. Nakao, "Determination of pore size and pore size distribution. 3. Filtration membranes", *Journal of Membrane Science*, 96 (1994), pp. 131–165.

L. Zeman et al., "Characterization of microfiltration membranes by image analysis of electron micrographs. Part I. Method development", *Journal of Membrane Science*, 71 (1992), pp. 221–231.

K. Kaneko, "Determination of pore size and pore size distribution. 1. Adsorbents and catalysts", *Journal of Membrane Science*, 96 (1994), pp. 59–89.

W. Müller, "New ion exchangers for the chromatography of biopolymers", *Journal of Chromatography*, 510 (1990) pp. 133–140.

S. Tsuneda et al., "Binding of Lysozyme onto a Cation–Exchange Microporous Membrane Containing Tentacle–Type Grafted Polymer Branches", *Biotechnol. Prog.*, 10 (1994), pp. 76–81.

S. Tsuneda et al., "High–throughput processing of proteins using a porous and tentacle anion–exchange membrane", *Journal of Chromatography A*, 689 (1995), pp. 211–218.

Ullmanns Encyklopädie der technischen Chemie, $4^{th}$ edition, vol. 10, pp. 475–561, Verlag Chemie, Weinheim 1975.

Yang et al., "Protein chromatography using a continuous stationary phase", *Journal of Chromatography*, 598 (1992), pp. 169–180.

S. Rippberger, "Mikrofiltration mit Membranen", pp. 19–21 and 128 and 129, Verlag VCH Weinheim 1992.

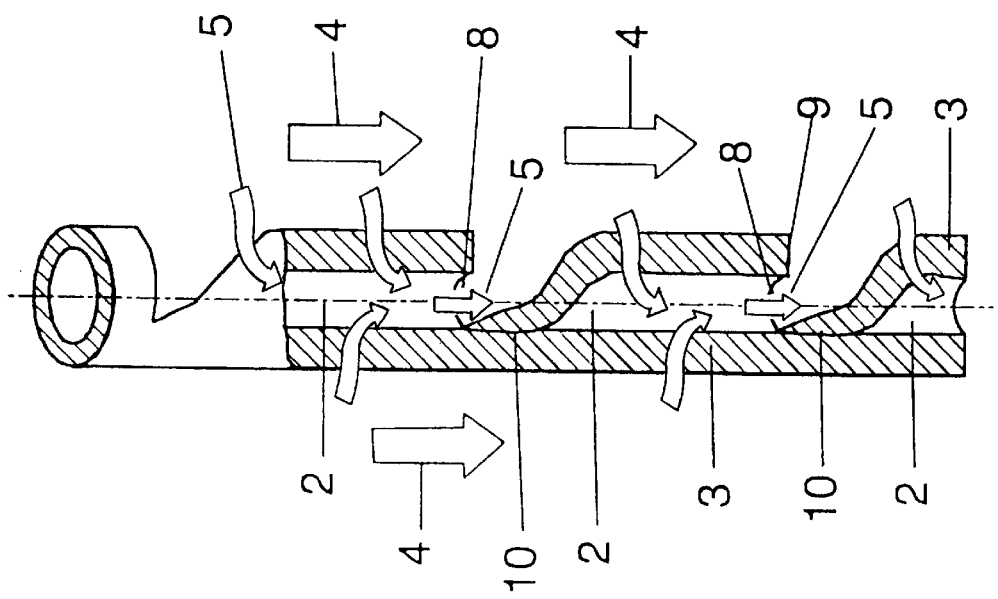

DEVICE AND PROCESS FOR THE SUBSTANCE-SPECIFIC TREATMENT OF FLUIDS

BACKGROUND OF THE INVENTION

1. Field of the Invention

The invention relates to a device for the substance-specific treatment of a fluid having a) a casing, b) an inlet arrangement for feeding the fluid to be treated into the casing, c) an outlet arrangement to remove the treated fluid from the casing and d) at least one treatment element for the substance-specific treatment of the fluid with one end facing the inlet arrangement and the other end facing the outlet arrangement, and the use of this device.

The invention also relates to a process for the substance-specific treatment of a fluid using a semipermeable membrane with a porous structure arranged in a casing, where the membrane has at least a first surface defining its exterior and at least a second surface defining its interior, comprising at least the steps:

a) feeding the fluid to be treated into the casing, b) causing the same fluid to flow through the casing, whereby the fluid to be treated is caused to flow along the exterior of the membrane as a primary stream but not along its interior, in such a fashion that a part of this primary stream flows as a secondary stream into the membrane via the exterior, through the membrane, where the substance-specific treatment of the fluid takes place on the part of the fluid to be treated which forms the secondary stream, and then flows out through the interior of the membrane, and c) removal of the treated fluid from the casing.

2. Discussion of Related Art

Substance-specific treatments of fluids are gaining an ever higher degree of importance in application fields such as biotechnology, medicine or chemical engineering. Examples of this are the recovery of active agents from cell suspensions in which genetically modified cells have produced substances such as antibodies, hormones, growth factors or enzymes, usually in small concentrations. An important application is also the extracorporeal removal of undesired substances from human blood. Finally, a broad field of application is the catalytic or biocatalytic—enzymatic—treatment of liquids such as the hydrolysis of oils by lipases which are immobilized on a matrix. In many applications for the treatment of liquids, these contain particles of many different kinds, i.e. they are suspensions.

The substance-specific treatment of fluids is often conducted such that the fluid to be treated is brought into contact with a carrier material on and/or in which interacting groups or substances are immobilized, which interact in specific, selective fashion with the target substance contained in the fluid, i.e., the substance targeted by the substance-specific treatment. Interactions of this kind may for example be cation or anion exchange, hydrophilic-hydrophobic interactions, hydrogen bonding, affinity or enzymatic or catalytic reactions, etc. In affinic substance separation, ligands are coupled to the carrier material or immobilized in the carrier material whose function it is to specifically bind a single target substance or a whole class of substances by adsorption. This target substance is termed a ligate. An example of a class-specific ligand are positively charged diethylaminoethyl (DEAE) groups or negatively charged sulfonic acid ($SO_3$) groups, which adsorb the class of positively charged or negatively charged molecules, respectively. One example of specific ligands are antibodies against a certain protein which is bound to the antibody as a ligate.

The basic criteria in the substance-specific treatment of fluids are productivity and selectivity. With regard to productivity, it is important that as many groups with a substance-specific action as possible which can interact with the target substance in the fluid to be treated are available per unit volume. A simultaneous aim is the maximization of the transport of the target substance to the groups or substances with a substance-specific action.

A carrier material for ligands which is frequently employed in affinity chromatography are sepharose particles to which the ligands are coupled and which are arranged in the form of a packing in a chromatographic column. Although it is possible by this means to achieve a high concentration of ligands with high selectivity, it is well-known that the productivity is low since due to the compressibility of the sepharose particles the flow through the column must remain relatively low. Moreover, the access of the ligates to the ligands contained in the sepharose particles is controlled by diffusion, so that especially for the separation of larger molecules such as proteins, due to their low diffusion rates the residence times are long, resulting in low throughput rates and low productivity.

U.S. Pat. No. 4,202,775 discloses a column material consisting of porous rigid polymer particles which can be used as adsorbents in the separation of organic components which are adsorbed on proteins present in aqueous solution. Although this column material no longer displays the disadvantage of compressibility, there remains the disadvantage of the diffusion-controlled substance transport in the particles, coupled with long residence times and low productivity.

In U.S. Pat. No. 5,019,270, a chromatographic column material made from rigid porous particles is presented in which a partial stream of the fluid to be treated and flowing through the chromatographic column flows through these particles by convection, whereby it comes into contact with the interacting groups in the porous structure of the particles and is then reunited with the liquid stream flowing around the particles. Due to the convective manner of the substance transport through the particles a reduction in the residence time and an increase in productivity is possible in comparison to the column material described earlier.

Although it is an advantage of chromatographic columns filled with particles of this kind that their structure and use is very simple, all particle-shaped column materials have the disadvantage in common that when treating liquids containing particles or cells, i.e. suspensions, the size of the particles of the column material selected must be relatively large in order to guarantee good flux through the particle packing without keeping back particles or, for instance, cells of the liquid, without any deep filtration effect through the packing, and in order to keep the pressure loss as low as possible. However, this means that the quantity of groups with a substance-specific action available per unit volume is reduced since the volume taken up by the particles in the column is smaller. In addition, increased particle size is associated with a detrimental prolongation of the residence time.

In chromatographic columns of this kind the goal is for the particles to be present in an ordered packing in the column, thus maximizing the proportion of particles in the packing and causing the flux between the particles to be more uniform. This can be partly achieved by using spherical particles with as uniform a diameter as possible. However, the manufacture of such uniform particles is laborious. In addition, when such particle packings are used it is generally not possible to prevent the shape of the flow channels between the particles from being non-optimal in fluid dynamic terms. In the gaps between the particles, it is easily possible for dead spaces to arise which can lead to negative phenomena particularly in the substance-specific treatment of suspensions such as the deposition of suspended particles in the gaps between the particles of the packing.

The described disadvantages of the particle-shaped carrier materials gave rise to the development of a series of processes for the substance-specific treatment of fluids in which membranes with a porous structure are employed as carrier materials for the interacting groups. Due to their porous structure, these membranes provide a large interior surface so that a large number of functional groups can be coupled onto the membranes in a high concentration per unit volume, which interact with the fluids to be treated flowing through the membrane. See, for example, E. Klein, "Affinity Membranes", John Wiley & Sons, Inc., 1991; S. Brandt et al, "Membrane-Based Affinity Technology for Commercial Scale Purifications", Bio/Technology Vol. 6. (1988) pp. 779–782.

By means of the design of the membrane used, it is possible to adapt it to the requirements of the treatment process. There are membranes in the form of hollow-fibers or flat membranes made from a wide variety of materials, so that it is possible to achieve an adaptation to the physico-chemical properties of the fluids to be treated. The pore size of the membranes can also be adjusted such that the fluid to be treated with the target substance it contains can flow through the membrane by convection and no blocking of the membrane occurs in case the target substance is bound to the interacting groups.

By means of the thickness of the membrane wall, the residence time of the fluid to be treated can be influenced, as can the pressure loss which arises as it flows through. Here, membranes are characterized by short transport distances for the fluid to be treated to the interacting groups, due to their usually small wall thickness (for example, $<100 \mu m$), which makes the residence times relatively short. At the same time a further advantage associated with the use of membranes as carrier materials as opposed to those in the form of particles is the more uniform flux through the carrier material due to the essentially uniform thickness of the membrane wall, and consequently a more narrow distribution of residence times as well as more uniform and more complete "utilization" of the interacting groups results.

A series of devices containing such membranes is described which are used in processes for the substance-specific treatment of fluids and in which both flat membranes and hollow-fiber membranes are employed. Here, so-called dead-end filtration or dead-end modules must be distinguished from cross-flow filtration or cross-flow modules.

In dead-end filtration, the entire fluid flowing into the membrane module as the feed stream is made to pass through the membrane and led off as a filtrate or permeate at the downstream side of the membrane opposite the upstream side.

In cross-flow filtration, the feed stream flows parallel to one side of the membrane, whereby part of the feed stream enters and flows through the membrane. The partial stream flowing through is led off as the permeate, and the partial stream remaining on the feed stream side is led off as the retentate. Here, an additional fluid stream can also be introduced on the permeate side of the membrane which takes up the partial stream flowing through the membrane.

In U.S. Pat. No. 4,935,142, a device for conducting an affinity separation process in dead-end fashion is described which contains piles of flat membranes. Coupled to the flat membranes are ligands to which the ligates to be separated from the fluid to be treated are bound. The flat membranes forming the membrane pile are sealed against the casing around them so that the stream is forced to flow through the membrane pile. The disadvantage of a construction of this kind is the high pressure loss on flowing through the pile, making additional measures also necessary to give the flat membrane elements adequate stability to withstand the high pressures which develop.

Also, in EP-A-0 173 500, EP-A-0 280 840 and EP-A-0 610 755, devices for use in membrane-based affinity separation processes, such as the isolation of immunoglobulins, antigens, etc., are described. These devices or membrane modules contain microporous flat membranes folded in the form of a star. The flat membranes folded in the form of a star are supported between two coarse meshes and positioned between two cylindrical casing elements which are arranged coaxially to each other. Preferably, several flat membranes folded in the form of a star are arranged concentrically to each other in the casing. Modules constructed in similar fashion are described in EP-A 0 662 340, whereby small particles with specifically interacting groups are incorporated into the folded flat membrane structure.

In the devices mentioned, the liquid to be treated is made to pass through the module from the inside to the outside or in the opposite direction under the force of pressure and at the same time in dead-end fashion flows through the membrane convectively. In contrast to modules with unfolded concentrically arranged membranes, the modules mentioned have the advantage that the membrane surface is larger while at the same time the pressure loss is lower. However, usually only low filling levels, defined as the membrane volume relative to the total volume of the module, are possible.

The disadvantage associated with all membrane modules run in dead-end fashion is that they are not suitable for the treatment of fluids containing particles, i.e., suspensions for example, if the particles contained in the fluid are of the magnitude of the pore diameter. The particles would cause a layer to form on the membrane wall and block the membrane. For use in affinity separation processes, for example, for liquids containing particles, i.e., suspensions, such dead-end modules can only be run in combination with a pre-filtration/pre-purification stage arranged in series in front. However, this means that the efficiency of a process of this kind is reduced, for instance due to the fact that a large part of the target substance is often lost in the pre-purification.

The disadvantages of modules run in dead-end fashion mentioned with regard to, for example, their use for suspensions can at least partly be avoided by using cross-flow modules. In these, the formation of a layer of suspended particles can be reduced by means of the feed stream flowing parallel to the membrane surface if the shear stresses are high enough.

WO 90/05018 discloses a membrane module for use in affinity separation processes whose construction corresponds to a cross-flow module. A liquid containing ligates is introduced into the module casing via an inlet arrangement and flows tangentially over one side of a membrane, which may for example be one made from hollow-fibers, to which ligands are coupled. Part of the liquid enters the membrane, flows through it, whereby the ligates are added to the ligands, and leaves as a permeate stream by the membrane side opposite the side it entered. Via separate outlet arrangements, the retentate stream and the permeate stream are led off. An essential characteristic of the membranes used in accordance with WO 90/05018 is an isotropic, microporous structure which makes a convection stream of solutions containing macromolecules possible.

In U.S. Pat. No. 4,266,026, a cross-flow module containing anisotropic hollow-fiber membranes is described for a process for conducting catalytic reactions. The catalysts used here are primarily enzymes which are immobilized in the membrane structure via coupling reagents, for example. The liquid to be treated flows as the feed stream under pressure through the lumen of the hollow fibers. Part of the liquid thereby flows convectively through the membrane wall and is subjected to the catalytic reaction. An example given is the catalytic conversion of lactose into glucose and galactose by means of galactosidase as a catalyst. The retentate and the permeate are led off from the module as separate streams of liquid, reunited in a storage container and recycled to the module on the lumen side until the desired turnover of the reacting substance has been reached.

A variation of a cross-flow process is described in WO 93/02777. For the specific removal of certain components from blood, a U-shaped bundle of semipermeable hollow-fiber membranes embedded in a specially shaped casing is employed, which acts as a plasma filter. The blood flows through the hollow-fiber membranes on the lumen side, and the blood plasma separated off by means of the membrane undergoes the substance-specific treatment in the exterior space around the hollow-fiber membranes. In this exterior space, there is a cleansing medium containing, for example, immobilized enzymes or antibodies for depositing the components to be separated. In principle the bundle can be divided up into an inlet arm and an outlet arm. Due to the positive transmembrane pressure arising in the area of the inlet arm, a convective transport of blood plasma (which superimposes diffusion) takes place through the membrane into the exterior space. In the area of the outlet arm, the treated plasma flows back into the lumen of the hollow-fiber membranes due to the negative transmembrane pressure arising there, and is reunited with the blood.

The advantage offered by the process according to WO 93/02777 is the fact that no separate pumps and/or regulatory organs are required for the permeate stream, i.e., the plasma stream. However, the modules used have a large volume of dead space in the exterior space of the membranes.

In the device for treating blood according to EP-A-0 112 094, the permeate is not removed separately from the module used either, but is reunited with the retentate, i.e. here, the blood, inside the module. Here, too, the membrane is being used as a plasma separator, a channel being formed from one side of the membrane through which the blood flows, and from the other side of the membrane and the casing surrounding it a treatment space is formed containing a material for the substance-specific treatment. By means of a suitable device, pressure variations are applied to the treatment space. This periodically changes the pressure difference between the blood channel and the treatment space such that, in alternate fashion, plasma firstly permeates from the blood through the membrane into the treatment space where it is subjected to the substance-specific treatment, and then the treated plasma flows in the opposite direction back through the membrane and is reunited with the blood.

A similar principle is pursued in WO 80/02805. According to this publication, too, part of the feed stream is made to pass by convection through the membrane and back again by means of pressure oscillations. In contrast to EP-A-0 112 094, in the device according to WO 80/02805, the biologically active material to which the target substance of the liquid to be treated is to be bound is coupled to the membrane in the pores and at the surface of the membrane, so that the substance-specific treatment of the liquid takes place while it is flowing through the membrane.

In EP-A-0 341 413, an adsorber module for the treatment of whole blood is described, in which blood flows in cross-flow fashion on the lumen side through the hollow-fiber membranes contained in the module which are equipped with ligands. Here, the plasma goes as a permeate through the hollow-fiber membrane wall into the exterior space around the hollow-fiber membranes, whereby the plasma is treated within the membrane wall. In a special embodiment, this module does not have any outlet for the permeate, but rather the plasma separated as the permeate is collected during the whole blood treatment in the exterior space around the capillaries and due to the pressure situations which arise passes through the hollow-fiber membrane wall again into the lumen of the hollow-fiber membrane. The disadvantage of a module design of this type, however, is that the plasma stream passing through the membrane can only to a limited extent be influenced. In addition, the necessary treatment times are relatively long, since filling up the exterior space around the hollow-fiber membrane itself requires permeate times of more than 10 minutes.

The modules described for the substance-specific treatment of liquids being run in cross-flow fashion have disadvantages such as the necessity for additional pumps and/or regulatory organs due to the separate permeate and retentate streams or additional aggregates for producing the pressure oscillations. They all have the disadvantage in common that the membranes must always be embedded in the casing, making manufacture of the membrane modules laborious. The effect of this is particularly negative if the substance-specific treatment makes it necessary to connect several modules in series. This is also important if for coupling or polymerizing of the ligands aggressive solvents such as toluene are used and this coupling takes place in the device. In practical use it has emerged that an embedding method providing the necessary resistance to the solvent is very laborious and expensive to achieve.

SUMMARY OF THE INVENTION

It is thus the object of the invention to make available a device for the substance-specific treatment of fluids in which the drawbacks of the state of the art are at least reduced, which can be manufactured simply, which can be adapted in a flexible manner to each fluid treatment desired and which is also suitable for clear solutions and especially for suspensions.

It is a further object of the invention to make available a process for the efficient substance-specific treatment of fluids using semipermeable membranes with a porous structure, which is also suitable for the treatment of suspensions.

These and other objects are achieved by a device for the substance-specific treatment of a fluid comprising a casing (25);

an inlet arrangement (24) for introducing the fluid to be treated (23) into the casing (25);

an outlet arrangement (28) to remove the treated fluid (27) from the casing (25); and at least one treatment element for the substance-specific treatment of the fluid with one end of the at least one treatment element facing the inlet arrangement and the other end facing the outlet arrangement, wherein the at least one treatment element of the device has at least one cavity which is optionally open at most in the direction of the outlet arrangement and which is formed by walls of the treatment element, wherein the walls of the at least one treatment element are formed at least partly from at least one semipermeable membrane with a porous structure and wherein the at least one treatment element is arranged in the casing in such a manner that between the inlet arrangement and the outlet arrangement, there is a continuous channel system touching the at least one treatment element and essentially surrounding the at least one treatment element at least at its end which is facing the inlet arrangement and its end which is facing the outlet arrangement.

These and other objects are further achieved by a process for the substance-specific treatment of a fluid using a semipermeable membrane with a porous structure arranged in a casing, whereby the membrane has at least a first surface defining its exterior and at least a second surface defining its interior, comprising at least the steps:

a) feeding the fluid to be treated into the casing, b) causing the same fluid to flow through the casing, whereby the fluid to be treated is caused to flow along the exterior of the membrane as a primary stream but not along its interior in such a fashion that a part of this primary stream flows as a secondary stream into the membrane via the exterior and then through the membrane, where the substance-specific treatment of the fluid takes place on the part of the fluid to be treated which forms the secondary stream, and then flows out through the interior of the membrane, and c) removing the treated fluid from the casing, in which process according to the invention over the entire extent on its exterior the membrane is flowed around essentially free by the primary stream and the secondary stream having passed through the membrane is reunited with the primary stream flowing along the exterior of the membrane after the substance-specific treatment.

BRIEF DESCRIPTION OF THE DRAWINGS

In simplified schematic fashion, the figures show the following:

FIG. 7: Embodiment of a treatment element made from a hollow-fiber membrane with several cavities which are open on one side arranged one behind the other;

DETAILED DESCRIPTION OF PREFERRED EMBODIMENTS

Figure 3:
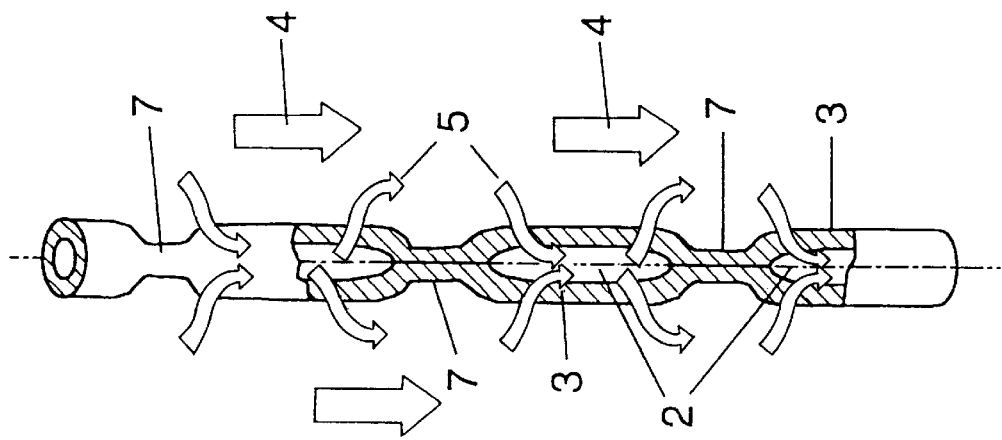
FIG. 3: Embodiment of a treatment element made from a hollow-fiber membrane with several closed cavities one behind the other.

For the purposes of the present invention, the term fluid is taken to mean gases, gas mixtures, gases charged with particles and liquids such as clear solutions or suspensions.

For the purposes of the present invention, the fluids to be treated are taken to mean fluids which contain certain substances or target substances to which the substance-specific treatment is directed.

The structure of the device in accordance with the invention is such that the fluid to be treated is introduced into the casing via the inlet arrangement and flows as a primary stream in the casing through the channel system in the direction of the outlet arrangement past the at least one treatment element arranged in the casing. Hereby, the at least one treatment element is positioned in the casing of the device in accordance with the invention without any embedding of the ends of the at least one treatment element being necessary, i.e., the end facing the inlet arrangement and that facing the outlet arrangement are free of any embedding surrounding the respective ends. By this means the primary flow is also able essentially to flow around the ends of the at least one treatment element.

Due to the pressure gradient generated by the flow in the channel system along the treatment element, part of the primary stream enters the treatment element as a secondary stream and flows through the semipermeable wall of the treatment element, in the process of which the substance-specific treatment with respect to the target substance takes place, and collects in the at least one cavity of the treatment element.

The cavities can be closed or open if at all only in the direction of the outlet arrangement. It was surprising to discover that even with closed cavities, a secondary stream forms through the treatment elements having cavities of this kind. A preferred embodiment of the device according to the invention has at least one cavity with an opening in the direction of the outlet arrangement which leads into the channel system.

If the cavity is closed, due to the pressure gradient the secondary stream enters the element through the semipermeable wall in the upper section of the treatment element which faces the inlet arrangement, collects in the cavity and due to the reduced pressure in the primary stream flows out of the cavity in the opposite direction through the semipermeable wall at the lower section of the treatment element which faces the outlet arrangement back into the channel system where it is reunited with the primary stream. Here, the substance-specific treatment of the fluid forming the partial stream can take place both on the first and second passage through the wall.

For the preferred embodiment in which at least one cavity has an opening in the direction of the outlet arrangement which leads into the channel system, the secondary stream essentially enters the treatment element along the whole extent of the treatment element between the inlet arrangement and the outlet arrangement with a diminishing gradient of the substance flow in the direction of the outlet arrangement. The entire secondary stream flowing through the semipermeable, porous wall collects in the cavity and flows at the lower end of the element through the opening back into the channel system, where it is reunited with the primary stream. The advantage of this embodiment of the cavity which is open in the direction of the outlet arrangement and linked to the channel system is that compared to a closed cavity, larger secondary streams, i.e., higher fluxes, through the wall of a treatment element arise, since the secondary stream does not have to overcome the flow resistance built up by the semipermeable wall of the treatment element.

The need for the cavity open at most in the direction of the outlet arrangement is the result of the applicability of the device in accordance with the invention to suspensions according to the task posed. For example, a treatment element with the cavity open in the direction of the inlet arrangement would act like a dead-end filter, the consequence of which would be that the suspended particles would be deposited in the cavity.

When dimensioning the cavity, it is important that flow resistance arising when the secondary stream flows through the cavity is small compared to the flow resistance arising when flowing through the semipermeable wall. At the same time the aim for each treatment element is for as high a proportion as possible of the volume of the treatment element to consist of semipermeable porous membrane wall, in which the substance-specific treatment takes place. A preferred ratio $V_w/V_t$ of the volume of the walls of a treatment element $V_w$ to the volume $V_t$ of the treatment element—consisting of the volume of the walls $V_w$ and the volume of the at least one cavity $V_c$—is in the range of, for example, $0.5<V_w/V_t<0.98$, an especially preferred ratio is in the range $0.6<V_w/V_t<0.85$.

Beside other influencing factors, the secondary stream flowing through a treatment element is determined by the pressure gradient dp/dx present along the treatment element. Here, dp is the differential pressure change along a differential length dx in the direction of the primary stream. The larger this pressure gradient, the larger is the secondary stream through the treatment element and the larger is in consequence the part of the primary stream which undergoes substance-specific treatment. The pressure gradient along a treatment element or along the channel system surrounding the treatment element increases with increasing throughput through the channel system, i.e., with increasing primary stream.

The pressure gradient dp/dx increases with increasing ratio $V_T/V_C$, which is termed degree of filling, where $V_T$ is the total volume of all treatment elements comprising the sum of volumes $V_t$ of the individual treatment elements and $V_C$ is the volume of the empty casing. A ratio $V_T/V_C$ between, for example, 0.4 and 0.95 has proven favorable, and a ratio between 0.55 and 0.75 has proven very favorable. With such degrees of filling, the spaces between the treatment elements and thus the corresponding dimensions of the cross-sections of the channels of the channel system are so small that in conjunction with suitable throughputs through or flow rates in the channel system, sufficiently high pressure gradients result to superimpose the diffusive transport through the porous membrane structure with a much larger convective transport due to the secondary stream.

It is expedient for the treatment element and its at least one cavity to have their longitudinal dimension in the direction of the flow through the casing. A dimension ratio L/D of the at least one cavity between 2 and 4000 is advantageous, where L is the dimension of the cavity in the direction of flow through the casing and D the hydraulic diameter of the cavity cross-section perpendicular to it. The hydraulic diameter D is defined here by the relationship D=4*A/C where A is the area of the aforementioned cross-section and C is its circumference. Dimension ratios L/D between 20 and 450 are especially advantageous.

Here, treatment elements are preferred whose walls have an essentially uniform thickness in their extension perpendicular to the direction of the primary stream. This also means that when flowing through the membrane the secondary stream at each point on a treatment element essentially flows the same distance, which is especially advantageous since it means the fluid to be treated will have as uniform as possible a residence time.

In the case of an arrangement of a single treatment element in the cross-section of the casing, it is necessary for the channel system to be formed between the treatment element and the inner wall of the casing, for instance by separate spacers or an appropriate shaping of the treatment element and/or the inner wall of the casing, whereby with regard to the flow around the treatment element being as uniform as possible the channel system should also be shaped as uniformly as possible.

With regard to the treatment of larger quantities of fluid, however, it is often expedient to put treatment elements together into groups of at least two, but preferably several treatment elements, where the treatment elements are arranged side by side essentially transverse to the direction of the extent of the channel system between the inlet arrangement and the outlet arrangement.

Here it is advantageous if the treatment elements put together to form a group are kept at a distance from one another by means of spacers, so that a channel system with defined channels is formed around the treatment elements, whereby the fluid can flow uniformly through the group of treatment elements and uniformly around the individual treatment elements. Furthermore, the size of the cross-sections of the flow channels can be adjusted by means of the spacers, making possible in the case of the substance-specific treatment of suspensions an adaptation to the size of the particles contained in the suspension and thus preventing the channel system being blocked up. At the same time, the pressure gradients resulting in the channels can be influenced via the flow cross-sections selected.

It is expedient for the spacers to be of a kind which has an elastic component. By this means such a group of treatment elements can be inserted easily into the casing, by first slightly pressing the group together, which will reduce the spacing between the treatment elements somewhat, inserting the group into the casing and then letting go, so that the spacing between the treatment elements increases once again. What is achieved in consequence is that the outer circumference of the group of treatment elements touches the inner wall of the casing, and an unwanted peripheral flow along the inner wall of the casing is at least reduced. A spacing between the treatment elements adjacent to the casing wall and the inner wall of the casing which is smaller than or equal to the spacing between the treatment elements is preferred.

The spacers can also be in the form of thin tubes or capillaries, whose axis is essentially parallel to the extent of the treatment elements of a group between the inlet arrangement and the outlet arrangement and in whose lumen the primary stream can flow through. It is preferable for these small tubes or capillaries not to be arranged along the entire extent of the treatment elements between the inlet arrangement and the outlet arrangement, but in a section of this extent at the end of the treatment elements facing the outlet arrangement. In this way the pressure drop of the primary stream can be increased and thus the secondary stream through the treatment elements.

Similar effects can also be achieved by appropriate shaping of the cross-section of the casing if the cross-section of the casing along a stage of treatment elements narrows in the direction of the outlet arrangement. By this means the spacing between the treatment elements at the ends facing the outlet arrangement is reduced compared to the spacing between the ends facing the inlet arrangement.

In order to increase the efficiency of the substance-specific treatment, it is an advantage if several treatment elements or groups of treatment elements are arranged in the casing as stages one behind the other in the direction of the extent of the channel system between the inlet arrangement and the outlet arrangement, i.e., in the direction of flow through the casing. By having a large number of stages arranged in series one behind the other, the dimension of the individual stage in the direction of the flow through the casing can be kept short and thus a change of the concentration of possible critical components in the fluid to be treated can be avoided. This is especially important in processes for the substance-specific treatment of suspensions in which at least part of the suspended particles is to be kept back by the semipermeable membrane wall of the treatment elements and at the same time too high concentrations of the suspended particles are to be avoided, for example in the substance-specific treatment of blood. By means of relatively short treatment elements, only a slight partial stream is taken from the primary stream along the treatment elements, so that the concentration changes remain low before the primary stream and secondary stream are subsequently reunited.

In the device according to the invention, the number of stages in the casing is preferably between 1 and 1000. A total of between 1 and 100 stages has proven favorable, a total of between 1 and 10 stages has proven most favorable. Here it is an advantage for the individual stages to be spaced apart in order to obstruct neither the primary stream nor the secondary stream locally by the next stage in the direction of the flow through the casing and in order to enable the primary stream and the secondary stream to be mixed well. A uniform mixing is advantageous in order for instance to avoid unwanted concentration fluctuations. Preferably, the ratio s/D of the spacing s between two consecutive stages to the hydraulic diameter D of the cavities of the treatment elements is between 0 and 5.

Naturally, in order to adapt to the requirements of the treatment process, it is possible to have several devices according to the invention in series one after the other, preferably containing several stages of treatment elements.

In the preferred embodiment of the invention, the secondary stream flows through the semipermeable wall of the treatment elements and by convection transports the target substance through the membrane. This requires the semipermeable membrane with a porous structure which is employed to shape the treatment elements to have a pore size which allows convective transport of the target substance through the membrane.

For a given pressure gradient in the channel system around a treatment element and for given geometrical dimensions of the treatment element, the secondary stream is of course maximized when the average pore size of the membrane is maximized. In the application, however, the size of the pore must be matched to the size of the target substance which may be in the form of dissolved macromolecules or possibly in the form of small particles with a particle size in the sub-micrometer range. At the same time, for example in the substance-specific treatment of suspensions, it will often be necessary for the membrane to have a separating function and to keep back components present in the suspension which are not target substances. This means that the pore size must not exceed a certain maximum. By this means the blockage of the pore system or, for example, undesired interactions in the membrane between such substances which are to be kept back and the groups with a substance-specific action provided to interact with the target substances can be prevented.

On the other hand, with regard to the applications of the device in accordance with the invention or to embodiments of the process in accordance with the invention described below, it may be more important to use membranes with the smallest possible pore sizes and the largest possible pore volumes or the greatest possible porosity, in order to provide the largest possible interior membrane surface for the substance-specific treatment. Preferably, the membranes applied in accordance with the invention have an average porosity of between 50 and 90% by volume. The average porosity means the ratio between the pore volume of the membrane and the membrane volume, the membrane volume comprising the pore volume and the volume of the material from which the membrane structure is made.

The demands made on the construction of the membrane, i.e., its structure and pore size distribution across the membrane thickness, arise from each specific substance-specific treatment application. The membrane structure can be isotropic across its thickness, i.e., within the membrane structure the pore diameters are essentially constant, they can be non-isotropic, symmetrical or even asymmetrical, and the membrane can have a layer with a much more dense pore structure on one of its sides, i.e., a skin. In the case of asymmetrical membranes, the denser layer can face the exterior of the treatment element or the cavity. For example, in the substance-specific treatment of suspensions, it may be necessary for the membrane to have a small pore diameter on the side facing the suspension in order to achieve a particular separation effect. In order at the same time to obtain the largest possible secondary stream through the membrane or the treatment element, however, it is expedient for the remaining membrane structure to have larger pores, but not too large depending on the application, to achieve the largest possible interior surface.

Membranes with an average pore diameter between, for example, 0.005 and 5 $\mu$m are preferred, while those with an average pore diameter between 0.1 and 3 $\mu$m are most preferred.

To determine the average pore diameter, different processes are employed depending on the size of the pore diameter and on the structure of the membrane. For essentially isotropic pore structures, pore diameters are determined by indirect means by a filtration experiment, in which an aqueous dextrane solution with a pre-determined size distribution of dextrane molecules is filtered through the membrane. From the relative quantity kept back which is measured as a function of the nominal molecule diameters the distribution of the pore diameters and thus the average pore diameter is calculated. This method is described for instance by K. Sakai, J. Membrane Science 96 (1994), 91–130, or by Shin-ichi Nakao, J. Membrane Science 96 (1994) 131–165, for dialysis or filtration membranes.

For non-isotropic membranes which for example have a layer with a denser pore structure, the cited determination method based on filtration experiments is also employed for determining the average pore diameter within the denser layer. For the determination of the average pore diameter of the areas of the non-isotropic membranes with larger pores, a visual analysis method according to L. Zeman et al, J. Membrane Science 71 (1992), 221–231 is employed. This is suitable for a pore diameter range between 0.1 and 5 $\mu$m, naturally both for isotropic and non-isotropic pore structures.

For applications of the device in accordance with the invention or the process in accordance with the invention for liquids such as, in particular, clear solutions or suspensions, it is an advantage if the membrane has an essentially constant average pore diameter along at least 80% of its dimension in the direction of its extent between the channel system and the at least one cavity, i.e., vertically to its exterior surface. By this means, a large interior surface combined with a large number of immobilized groups with a substance-specific action can be achieved with a simultaneous low pressure loss on flowing through the membrane perpendicularly to its surface and thus a large secondary stream. An essentially constant average pore diameter is taken to mean one which does not change by more than +/−50% along the aforementioned extent of the membrane.

For the substance-specific treatment of suspensions, it proves advantageous to use a membrane which has a layer on the side facing the channel system which has a smaller average pore diameter than the adjacent region of the membrane in the direction toward the cavity with an essentially constant average pore diameter. It is advantageous if this layer is between 1 $\mu$m and 5 $\mu$m thick and has an average pore diameter which is smaller by a factor of 5 to 50 than the average pore diameter in the adjacent region.

In the device in accordance with the invention or in the device for conducting the process in accordance with the invention, the use of porous membranes with a large interior surface is preferred. Porous membranes with a BET surface between 2 and 300 m$^2$ per cm$^3$ membrane volume have proven favorable, while membranes with a BET surface between 4 and 30 m$^2$ per cm$^3$ membrane volume have proven most favorable. The BET method which is based on nitrogen adsorption measurement for the determination of the surface of porous membrane structures is described by K. Kaneko, J. Membrane Science 96 (1994), 59–89.

In the present invention, the use of hollow-fiber membranes or flat membranes is preferred in order to form the treatment elements. However, other membrane forms such as membrane tubes or membrane pipes are also included.

In the preferred use of hollow-fiber membranes, the wall of the hollow-fiber membrane is also the wall of the at least one cavity of the treatment element and at least one of the ends of the hollow-fiber membrane is closed. The cavity is formed by the lumen of the hollow-fiber membrane and bounded by the interior of the hollow-fiber membrane.

By simple means, treatment elements of the present invention may be manufactured from hollow-fiber membranes. By closing both ends or only one end of hollow-fiber membrane sections, for example by welding it or them shut, treatment elements with cavities which are closed or open on one side can be manufactured. By folding hollow-fiber membrane sections perpendicularly to the longitudinal axis, depending on how this is done, treatment elements with two cavities open on one side or treatment elements with one cavity which has two openings facing the same direction can be produced. Such treatment elements must be inserted into the casing of the device in accordance with the invention in such a way that the openings face in the direction of the outlet arrangement of the device and the treatment elements are always closed in the direction of the inlet arrangement.

Hollow-fiber membranes with various external contours, i.e., with different external outlines viewed in cross-section, may be employed. The hollow-fiber membranes may, for example, have an essentially round or circular, triangular, rectangular, hexagonal or octagonal contour, or they can be oval, elliptical, three-lobed or four-lobed, etc. For application in the device in accordance with the invention or to conduct the process in accordance with the invention, hollow-fiber membranes have proven favorable which have a wall thickness between, for example, 15 $\mu$m and 500 $\mu$m. Most favorable are membranes having a wall thickness between 100 $\mu$m and 300 $\mu$m. It is preferable for the hydraulic diameter of the hollow-fiber membranes employed to be between, for example, 50 $\mu$m and 900 $\mu$m. Especially preferred are hollow-fiber membranes with a hydraulic diameter between 200 $\mu$m and 400 $\mu$m.

It is advantageous if the hollow-fiber membranes are put together in at least one group of adjacent treatment elements whereby the hollow-fiber membranes of this group are kept apart by textile threads. In principle it is sufficient here to lay the textile threads between the hollow-fiber membranes. However, it is preferable for the hollow-fiber membranes of a group to be bound by means of the textile threads into at least one hollow-fiber mat. Such mats can be manufactured advantageously by well-known processes as knitted mats, woven mats or woven tapes, but also as crocheted mats. In the case of weaving or knitting, the textile threads are the weave or knit threads which run cross-wise to the hollow-fiber membranes. By means of these cross-wise threads, the hollow-fiber membranes are kept in advantageous manner at equal distances from each other and within the mats are arranged essentially parallel to each other. By means of such mats, groups of adjacent treatment elements can be manufactured which have a high degree of order and in which there is a uniform channel system between the treatment elements.

Such mats of treatment elements made from hollow-fiber membranes can for example be spirally wound up in a single layer or multiple layers according to known processes to form bundles or be layered on top of each other to form stacks of single mat layers or folded mat layers. It is expedient for the single laps or the single layers to be kept apart, e.g. by means of the woven-in or knitted-in threads and possibly by means of additional spacers introduced between the single lap layers, for example in the form of nonwoven or woven fabrics permeable to fluids.

The groups of hollow-fiber membranes manufactured thus are then inserted into the casing of the device in accordance with the invention. Here, it is an advantage if there is an elastic component in the spacers, such as that occurring in nonwoven fabrics due to reversible compressibility of the nonwovens, and this makes insertion of the groups into the casing simpler. Preferably, bundles are employed in which at least one hollow-fiber mat is spirally wound around an axis or a core parallel to the direction of the extent of the channel system between the inlet arrangement and the outlet arrangement of the device. A further advantageous embodiment are bundles in which at least two hollow-fiber mats are laid on top of each other and spirally wound around an axis or a core parallel to the direction of the aforementioned extent of the channel system, whereby the hollow-fiber mats are laid on top of each other such that the hollow fibers of the hollow-fiber mats laid on top of each other are brought into a criss-cross arrangement. The manufacture of such bundles is described in detail in EP 285 812. For such bundles, the angle between the hollow-fiber membranes arranged in a criss-cross pattern can be between, for example, 0° and 120°, angles between 30° and 90° have proven favorable.

It is also possible in simple fashion to manufacture treatment elements with more than one cavity from hollow-fiber membranes. Hollow-fiber membrane sections of suitable length can for example be pressed together or welded at several points along their longitudinal axis, so that several closed cavities lying one after the other are separated off. In similar fashion, it is also possible to achieve several open cavities, by partially cutting into the hollow-fiber membrane at several points along its longitudinal axis perpendicular to the latter, whereby—relative to the state of a treatment element thus manufactured in the device—the cutting edge in the direction of the outlet arrangement is welded to the remaining membrane wall in order thus to close the cavities in the direction of the inlet arrangement.

According to a further preferred embodiment of the invention the at least one treatment element is formed from at least one flat membrane. Such a treatment element can for example be manufactured by folding a rectangular or quadratic piece of a flat membrane, for example in a U-shape. The two resulting arms of the flat membrane folded in a U-shape are kept apart in order to form the at least one cavity. For the spacer, a material which is permeable to fluids such as a nonwoven or a woven material can be employed.

According to a further advantageous embodiment of a treatment element made from flat membranes, two flat membranes arranged parallel to each other and kept apart from one another are joined, for example by welding together positively at least along the edge which faces in the direction of the inlet arrangement, so that the arms of the treatment element are formed from the flat membranes. The two flat membranes used can be the same, but they can also be different, for instance as to their material, their structure or the groups with a substance-specific action provided for interaction with the target substances. One of the two flat membranes can also be substituted by a sheet which is for example impermeable to fluids, where this appears to be an advantage—for instance for reasons of the stability of the treatment elements or from a manufacturing point of view.

In such treatment elements, the side of the membrane or the sheet, if employed, surrounding the cavity is defined as the interior and the side facing outwards defined as the exterior of the membrane or the sheet, if employed.

The flat membranes used in the device in accordance with the invention or to conduct the process in accordance with the invention preferably have a wall thickness between 15 and 500 $\mu$m, especially preferable are flat membranes with a wall thickness between 100 $\mu$m and 300 $\mu$m.

It is expedient for the two sides of the treatment element continuous to the fold edge or to the edge closed positively to be also closed, e.g., by welding. Treatment elements made from flat membranes which are open at the sides are not recommended for use in the application due to possible leak and short-circuit streams. The edge opposite to the fold edge can also be closed in order to make a closed cavity. However, it is advantageous if it remains open in order to make a cavity which is open on one side, whereby in this case the treatment element manufactured thus must be inserted into the casing of the device in accordance with the invention such that the opening faces in the direction of the outlet arrangement of the casing.

Treatment elements manufactured in this fashion can be employed in a flat form, whereby it is preferable for several of these flat treatment elements to be layered side by side in a stack to form groups. It is expedient to use a material permeable to fluids to keep the treatment elements of a group apart from each other and to keep a space between the inner wall of the casing and the treatment elements adjacent to it, a material such as a woven material or a nonwoven, for example, in which in particular in the substance-specific treatment of suspensions high demands are made in terms of permeability. This permeable material therefore keeps the exteriors of the membranes and the sheets, if used, apart and in addition builds up an additional pressure gradient in the flow direction of the primary stream, which influences the size of the secondary stream.

The spacers which are used, as described above, to provide a definite spacing between the arms of the treatment elements which are at least partly formed from flat membranes, between the treatment elements of a group and between the inner wall of the casing and the treatment elements adjacent to it and which at the same time are to be permeable to fluids, can be formed as separate elements. However, the function of the spacer at the interior and/or exterior of the membrane and/or the sheet if there is one joined to the membrane can also be integrated into the membrane or the sheet itself, for example by means of surface structures with grooves, nubs or other profiles.

Groups of treatment elements made from flat membranes can be manufactured for example by pleating a three-ply flat laminate which consists of a flat spacer, for instance in the form of a permeable nonwoven, a centrally positioned flat membrane layer and a further spacer layer. By pleating this three-layered laminate together, a flat pleated product is formed from which groups of treatment elements arranged side by side made from flat membranes folded in a U-shape are formed by subsequent cutting open, for example centrally, with regard to the plane of the pleated product. In order to make processing better, the three layers of the laminate can for example also be joined together in points.

An embodiment has proven favorable in which the fold edges of the treatment elements of two consecutive stages of the device in accordance with the invention viewed in the direction of the extent of the channel system between the inlet arrangement and the outlet arrangement form an angle between 5° and 175°. Preferred angles are 30°, 45° or 90°. In this way, improved mixing of the primary stream with the secondary stream is achieved after each stage and the formation of a peripheral flow between the treatment elements and the inner wall of the casing is reduced. The spacing between the stages can be minimized and is preferably such that the ratio s/D of the spacing s between two adjacent stages and the hydraulic diameter D of the cavity of the treatment element is between 0 and 1.

It is also possible in simple fashion to manufacture from flat membranes treatment elements with several cavities one behind the other. Flat-membrane treatment elements of suitable length measured in the direction of flow through the casing of the device in accordance with the invention can for instance be pressed together or welded together at several points perpendicular to their longitudinal axis, whereby several cavities lying one behind the other which are closed and supported by spacers are formed. In similar fashion it is also possible to achieve several cavities one behind the other open in the direction of the outlet arrangement, by cutting through the treatment elements at several points along their longitudinal axis perpendicular to the latter on one of their arms, and by welding or gluing to the remaining arm the cutting edge lying in the direction of the outlet arrangement in order to close the cavities in the direction of the inlet arrangement.

The flat treatment elements described can also be further processed to give spirally wound treatment elements, whereby for example winding is performed spirally around one axis or one core perpendicularly to the fold edge or the edge closed positively. Between the single laps it is an advantage for spacers to be inserted whereby the same conditions apply for the spacing between the single laps as for the spacing between two flat treatment elements made from flat membranes. Such treatment elements wound up spirally are then advantageously arranged in a casing such that the direction of the winding axis and the through-flow direction of the casing match. If the spiral-shaped treatment element has an open edge it will then face in the direction of the outlet arrangement of the casing.

The inner cross-section of the casing in which the treatment elements put together to form groups or the stages of treatment elements are arranged can be any shape. However, for hollow-fiber membranes and flat membranes, it is preferable for the casings used to have a quadratic, rectangular, hexagonal, octagonal or possibly round inner cross-section.

Into this casing, the treatment elements or groups of treatment elements, which preferably have spacers with an elastic component, are inserted under slight compression and positioned under relaxation in the casing. In the case of flat treatment elements made of flat membranes, depending on the shape of the casing's inner cross-section, it is simple to adjust definite angles between the fold edges of the individual stages in the casing.

In the case of treatment elements made from hollow-fiber membranes, depending on the application, an injection needle or a canulla may be suitable for a casing, in which for example several stages of single treatment elements can also be arranged one behind the other. For other applications a flexible casing, for example made from an elastic tube, has proven advantageous. In order to make it easier to insert the treatment elements or the groups or stages of treatment elements, the casing can be made so as to be able to be shrunk radially, whereby the shrinking is performed after the treatment elements have been inserted. Especially in the case of casings which are long relative to their diameter, it can be an advantage for the casing to be shaped or wound in the form of a helix or spiral.

In many cases, no fixed junction between the treatment elements and the casing is necessary. However, in special cases it is also possible, for example by means of polyurethane, epoxy resin, thermoplastic or similar material, to join in a fixed manner the treatment elements of a group or stage which are adjacent to the inner wall of the casing, at least partly. By this means it can be ensured that the individual group of treatment elements is positioned in stable fashion, but above all it is at least possible to reduce the peripheral flow between the inner wall of the casing and the treatment elements and to compensate for unevenness in the outer contour of groups of treatment elements. In addition, by this means for instance the flat membrane treatment elements described can be sealed at their fronts, i.e., at the edges adjacent to the fold edge, or the edge closed positively. Suitable methods to join the treatment elements thus with the casing are described for example in EP-A-521 495.

The process in accordance with the invention can be employed for a wide variety of substance-specific treatments of fluids. Here especially good results are achieved in the treatment if in these processes in accordance with the invention the device in accordance with the invention is used, whereby it is preferable for there to be groups with a substance-specific action immobilized on and/or in the membrane. With reference to the particular treatment process, different groups with a substance-specific action can be immobilized on and/or in the membranes, which interact in a specific manner with the various target substances contained in the fluid to be treated. In the same way it is also possible for different membranes each with a different group with a substance-specific action to be employed together.

In a preferred embodiment of the process in accordance with the invention, the fluid to be treated is recirculated and passes through the treatment process several times until the degree of treatment desired has been achieved. Suspensions containing particles are preferably used as the fluids to be treated in such embodiment.

According to an especially preferred embodiment of the invention, the groups with a substance-specific action are ligands for affinity separation of ligates from fluids to be treated, or they are enzymes or catalysts. Preferred processes in accordance with the invention are processes for the purification/separation of ligates from a liquid containing ligates, where membranes are selected on and/or in which ligands for the aforementioned ligates are immobilized, as well as processes for the enzymatic treatment of liquids, where membranes are selected on and/or in which enzymes are immobilized, and processes for the catalytic treatment of liquids, where membranes are selected on and/or in which catalysts are immobilized.

For the immobilization of groups with a substance-specific action on and/or in the membranes, the processes described in the literature can be employed. With regard to which groups with a substance-specific action can be used in the fluid treatment concerned, it is also possible to fall back on those described in the literature. Several different options for the immobilization of the groups with a substance-specific action are possible, both with regard to the place where they are immobilized and with regard to the manner in which they are immobilized.

Thus, these groups with a substance-specific action can be coupled to the membrane in adsorptive manner or via covalent binding. This coupling to the membrane can be performed both before insertion into the casing and after insertion of the membrane as the treatment element into the casing of the device in accordance with the invention. Here, depending on the application concerned, the groups with a substance-specific action can be for example coupled in an essentially homogeneous fashion to the entire surface of the porous membrane, i.e., both on the exterior and on the interior surface formed by the pores, i.e., immobilized on and in the membrane. However, it may be necessary for the groups with a substance-specific action to be immobilized only on a part of these surfaces, for instance if single components of the fluid to be treated are not supposed to come into contact with the groups with a substance-specific action. In such a case it is expedient for one thing to avoid transport of these components through the membrane to the immobilized groups with a substance-specific action by means of the selection of a membrane with a suitable cutoff. For another, it is also then necessary to keep the surface of the membrane which faces the primary stream, i.e., the fluid containing these components, free from the groups with a substance-specific action. This can be achieved for instance by passivating this surface, for example by plasma treatment before the groups with a substance-specific action are coupled on.

However, groups with a substance-specific action can also be directly built into the membrane matrix, in the case of membranes made from polymer materials for instance by modification of the polymer material with ionic, hydrophilic or hydrophobic groups, for example, or by the use of polymer blends in which at least one polymer component has groups with a substance-specific action.

A further possibility consists in incorporating such groups with a substance-specific action or carrier substances containing such groups or particles into the pore system of a membrane during the manufacturing process for the membrane or in, for example, flooding them into the finished membrane at a later stage. In the latter case, it is expedient for the membrane to have an asymmetrical structure and possibly a skin, where the openings of the skin or the pores of the fine-pored side of the membrane are dimensioned such that the groups with a substance-specific action or the aforementioned carrier substances or particles cannot pass through. Here, the flooding in and the subsequent substance-specific treatment of the fluid is performed in such a manner that the material streams enter the membrane from the more open-pored side of the membrane and thus the substances or particles carrying the groups with a substance-specific action are kept back by the less open-pored side. It is expedient for such systems where groups with a substance-specific action have been flooded in to be employed in conjunction with treatment elements which are open in the direction of the outlet means of the device containing the treatment elements.

In each case, the size of the pores must be selected such that despite the groups with a substance-specific action immobilized in the pores, the target substances can be transported through the membrane convectively by at least part of the fluid to be treated.

With regard to the material from which the membrane in accordance with the invention is made, there are no restrictions. Thus, membranes made from inorganic materials such as glass, ceramics, $SiO_2$, carbon or metal, from organic polymers or mixtures of the same may be employed. The polymers may have a hydrophilic and/or hydrophobic character, they can be selected from the group of cellulosic polymers such as cellulose or regenerated cellulose, modified cellulose, such as cellulose ester, cellulose ether, amine-modified celluloses and mixtures of cellulosic polymers, from the group of synthetic polymers such as polyacrylonitrile and corresponding copolymers, polymers containing polyurethane, polyaryl sulfones and polyaryl ether sulphones such as polysulfone or polyethersulfone, polyvinylidene fluoride, polytetrafluoroethylene, water-insoluble polyvinyl alcohols, aliphatic and aromatic polyamides, polyimides, polyether imides, polyester, polycarbonates, polyolefins such as polyethylene, polypropylenes, polyvinyl chloride, poly(phenylene oxide), polybenzimidazole and polybenzimidazolones, as well as modifications, blends, mixtures or copolymers obtained from these polymers. To these polymers or polymer mixtures further polymers such as poly(ethylene oxide), polyhydroxy ether, poly(ethylene glycol), polyvinylpyrrolidone, poly(vinyl alcohol) or polycaprolactone, or inorganic substances such as $SiO_2$ may be added as additives. In some cases the membrane may, for example, have been subjected to a surface modification, in order to adjust certain properties of the membrane surface, for example in the form of certain functional groups.

Experience with membranes made of polymers which withstand solvents and maintain pH values has been particularly good, especially with membranes made from polytetrafluoroethylene or polyvinylidene fluoride and the modifications, blends, mixtures or copolymers obtained therefrom. Such membranes are described for example in DE-A-39 23 128.

For the purification/separation of ligates from a liquid containing ligates by means of affinity separation or affinity chromatography, a large number of applications are known. Here, what is meant by affinity chromatography is biospecific adsorption as well as separation processes such as, for example ion exchange chromatography, metal chelate chromatography, hydrophobic chromatography, covalent chromatography or the direct sorption of molecules on a specific adsorber material.

Interesting applications refer to the purification of monoclonal liquids, the removal of proteases for the stabilization of biological liquids, the recovery or therapeutic removal of blood plasma components from blood plasma or whole blood, the removal of pyrogens from biological or pharmaceutical liquids, the separation of enantiomers or the isolation of enzymes, to name but a few examples.

Further applications are found in the field of cell selection. In these, use can be made of the feature that when the device in accordance with the invention is used or in conducting the process in accordance with the invention part of the primary stream flows as the secondary stream towards the membrane wall of the treatment elements and through the walls of the treatment elements. The advantage of this when cell suspensions are used is that cells which are target substances are transported by convection to the membranes and are there brought into direct contact with, for example, ligands immobilized on the exterior of the membrane or the treatment element, which for example identify a certain surface protein of the cells. The devices in accordance with the invention are also most suitable for applications in the field of genetic technology, if such applications call for convective transport for example of genes for instance to viruses or cells immobilized on and/or in the membrane.

In the sense used here, depending on the application, ligands can have a non-specific, group-specific or specific action (see E. Klein, "Affinity Membranes", John Wiley & Sons, Inc., 1991). Such ligands are, for example, monoclonal antibodies, polyclonal antibodies, peptides, antigenic substances, glycoproteins, Protein A, Protein G, enzymes, receptor proteins, growth factors for cells, hormones, regulatory proteins, inhibitors, cofactors, heparin, protamine, poly-l-lysines, biotin, avidin, amino acids such as tryptophan, phenylamines, L-histidine or antibiotics. In addition, the ligands can also be salts such as $Fe_4[Fe(CN)_6]_3$ or colorants. However, they can also be hydrophilic groups or ionic groups in the surface of the membrane material itself or polymers bound to the surface. Reference can be made for example to the examples given in WO 90/04609, WO 90/05018 and EP-A-0 565 978 or those given in E. Klein, "Affinity Membranes", John Wiley & Sons, Inc., 1991, without restricting the possibilities to these.

Without enumerating all possibilities exhaustively here, the ligands can, for example, be produced by surface modification of the membrane, they can be bound to the surface directly or via spacer molecules, and they can also be bound to the surface via tentacle systems or chains, whereby a plurality of ligands can be bound to each chain or each tentacle system.

In order to increase the capacity particularly of ion exchange membranes, various methods known per se can be applied, whereby the number of ion groups, i.e., the ligands on the pore surface of the membranes, is increased. It is preferable for the ligands to be coupled to the membrane via molecules of long-chain linear polymers, whereby the molecules of the long-chain linear polymers carry several ligands. The use of long-chain linear polymers, so-called tentacles, on whose arms the ligands sit, is described for example by W. Müller, J. Chromatogr., Vol. 510 (1990), p. 133. The manufacture of such tentacles is described for example in Tsuneda et. al. (Biotechnol. Prog., Vol. 10 (1994), pp. 76–81 and J. Chromatogr. Vol. A 689 (1995), pp. 211–218) and can be performed via the radiation-induced graft polymerization of a monomer containing an epoxy group, such as glycidyl methacrylate, with subsequent chemical conversion into $SO_3H$ groups or diethylamino groups. A different process for the grafting of polymer flat membranes containing nitrogen which can be employed to increase the ion exchange capacity of the membrane treatment elements in accordance with the invention is described in EP-A-0 490 940.

Membranes which contain polyamides derivatized with polymerizable double bonds according to DE-OS-195 01 726 are very well suited for the device in accordance with the invention or for conducting the process in accordance with the invention. These derivatized polyamides can be obtained by converting the polyamide in an aqueous solution with a compound containing both a polymerizable double bond and an oxirane ring, and can be converted to block polymerisates with improved properties.

For applications in the field of the enzymatic or general catalytic treatment of liquids, membranes can be selected on and/or in which according to methods known per se enzymes or catalysts are immobilized.

Applications in the field of the enzymatic treatment of liquids are, for example, the enzymatic esterification of ethylglycoside, the enzymatic hydrolyzation of starch via amyloglucosidase, the enzymatic hydrolyzation of enantiomers, vegetable oils, animal oils such as fish oil or triglycerides via lipases, the enzymatic decomposition of proteins via proteinases, the lactose decomposition in milk via lactase or the decomposition of blood components via appropriate enzymes such as urea via urease. Also, applications such as described in U.S. Pat. No. 4,061,141, for example, belong to this field. Other enzymes and their use and how they may be immobilized are described in Ullmann's Encyklopädie der technischen Chemie, 4th edition, Vol. 10, pp. 475–561, published by Verlag Chemie Weinheim 1975. Information on catalysts and their immobilization in membrane structures which can also be used in the present invention may be found for example in U.S. Pat. No. 4,266,026.

In the invention, the cavities can be filled partially or completely with functional elements without thereby losing their actual collection and channel function for the secondary stream. In a simple case, the kind of functional elements as described above can be present in the form of a nonwoven permeable to fluids and only perform the function of a spacer. However, nonwovens can be employed in which particles have additionally been introduced which in turn carry substance-specific groups, for example in the form of ligands or enzymes. Other examples are woven fabrics or nonwovens containing activated carbon or activated carbon on its own. It is also conceivable to introduce living cells into the cavities, which produce or convert suitable biologically active molecules during the substance-specific treatment of a liquid.

In the same fashion, the spacers located between the treatment elements can also fulfill other functions apart from their function as spacers. For example, groups with a substance-specific action can be immobilized on and/or in the porous membrane wall of the treatment elements as well as additionally on the spacers. For this purpose it is expedient for the spacers to be made of the same polymer or the same polymer family as the membrane material. Particularly in the case of the spacers introduced between treatment elements made from flat membranes and between the mats made from hollow-fiber membrane elements, textile woven fabrics such as those described for example by Y. Yang et al., J. Chromatographie 598 (1992), 169–180, have proven favorable. Here, fabrics with multifilament threads with a single thread diameter between 1 $\mu$m and 30 $\mu$m lead to especially good results. Fabrics which have both the warp and the weft threads lying at an angle of between 30° and 60° to the direction of the primary stream have proven satisfactory. The spacers on the primary stream side can also differ from those in the cavities and if, for example, suspensions are employed, can be woven less densely.

The invention will be described in more detail below with reference to the figures.

Figure 2:
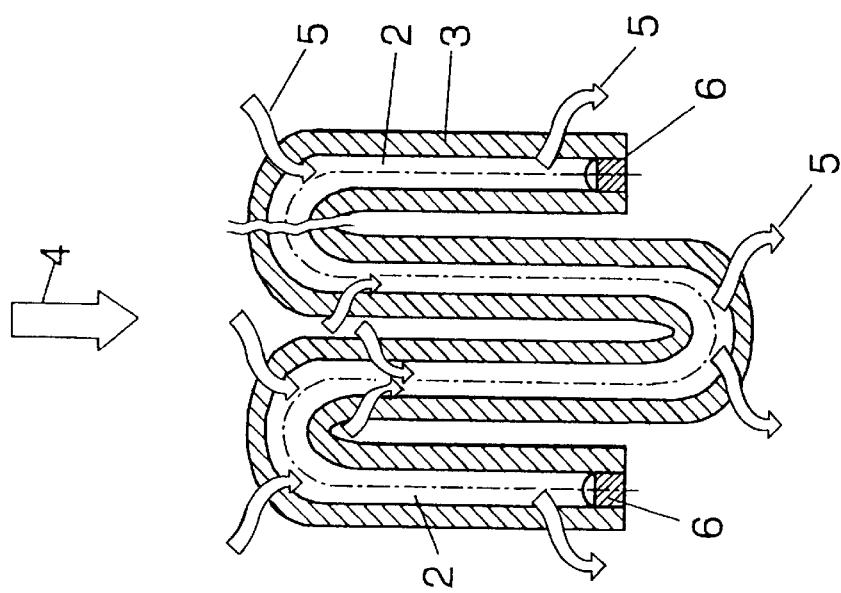
FIG. 2: Embodiment of a treatment element with a closed cavity made from a hollow-fiber membrane, laid in hairpin bends.
Figure 1:
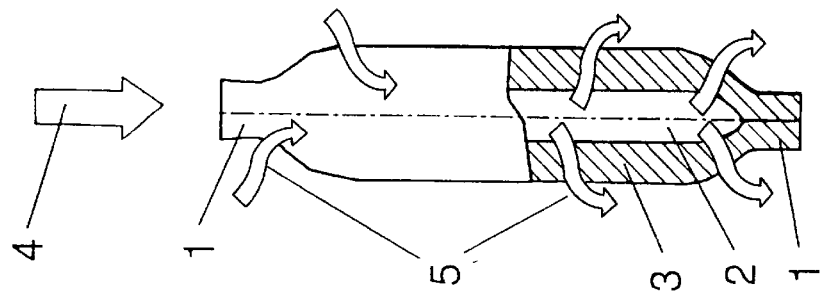
FIG. 1: Embodiment of a treatment element with a closed cavity made from a hollow-fiber membrane, welded ends.
Figure 4:
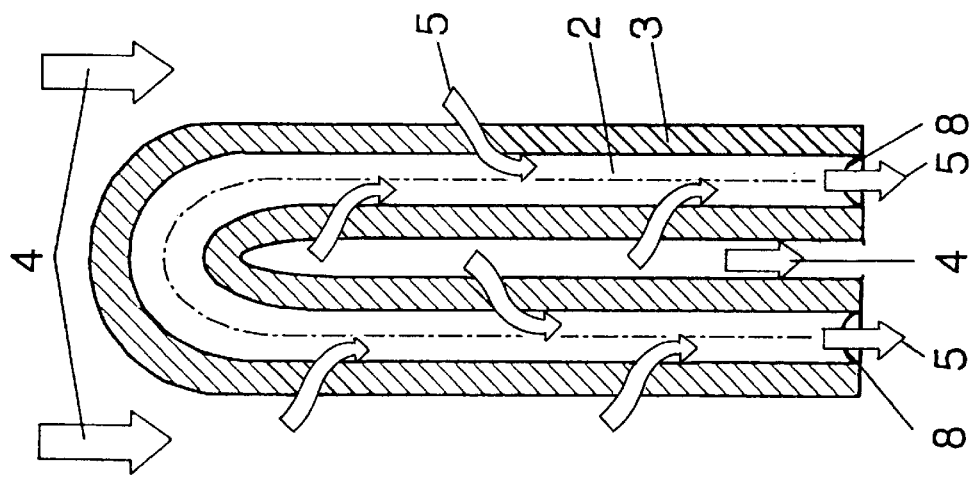
FIG. 4: Embodiment of a treatment element made from a hollow-fiber membrane with a cavity open on one side, one end of which is glued together.

FIGS. 1 to 3 show various embodiments of treatment elements which can be manufactured from hollow-fiber membranes and which have closed cavities. Here, FIG. 1 shows an element, partly depicted in cross-section, which was manufactured from a section of a hollow-fiber membrane of appropriate dimensions by welding the two ends 1 of this section. The cavity 2 is formed by the lumen of the hollow-fiber membrane, the wall 3 of the treatment element is simultaneously the wall of the hollow-fiber membrane. The arrows indicate the primary stream 4 and the secondary stream 5. The primary stream runs in the direction of the longitudinal extent of the treatment element, the secondary stream 5 enters the treatment element at the upper section of the treatment element lying opposite to the direction of the primary stream, collects in the cavity 2 and leaves the treatment element in the lower section of the treatment element in the direction of the primary stream.

The treatment element according to FIG. 2 can be obtained from a hollow-fiber membrane which has been laid in several hairpin bends one after the other. In this example the ends of the hollow-fiber element are provided with a stopper 6 such as can be obtained for example by dipping the ends in a casting material or by filling them with a hot-melt adhesive. It is naturally also possible to weld the ends shut. In the example depicted, the cavity 2 runs across the entire length of the hollow-fiber membrane section. In similar fashion, however, treatment elements can be manufactured by folding down the hollow-fiber membrane at the bends so that they then have partial cavities closed where it has been folded down. As for the treatment element in FIG. 1, the primary stream 4 and the secondary stream 5 are depicted for this treatment element according to FIG. 2.

The embodiment shown in FIG. 3 is an example of a treatment element with several closed cavities 2 one behind the other in the direction of the primary stream. An element of this kind can be manufactured, for example, by welding shut a hollow-fiber membrane section of appropriate dimensions at several points 7 along its longitudinal axis.

Figure 5:
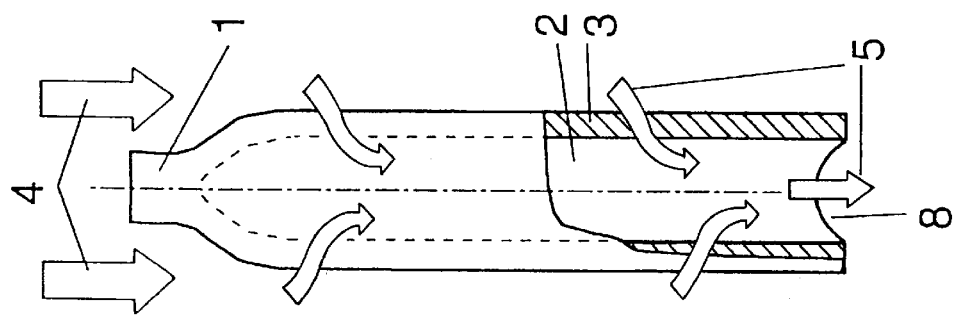
FIG. 5: Embodiment of a treatment element made from a hollow-fiber membrane with a cavity open on one side, one end of which is welded together.

In FIGS. 4 to 7, various embodiments of hollow-fiber membrane treatment elements are shown which have cavities open on one side, where these treatment elements are built into a casing in accordance with the invention in such a manner that the opening 8 of the cavities open on one side faces in the direction of the outlet means, i.e., in the direction of the flow of the primary stream 4 through the casing. The embodiment according to FIG. 4 can be manufactured from appropriate lengths of hollow-fiber membranes by closing the one end of the hollow-fiber membrane section with a stopper 6, for example by means of a hot-melt adhesive or by dipping the end into a casting material. The embodiment in FIG. 5 represents an element of essentially the same type, in which however the one end 1 has been closed by welding. In the built-in state, part of the primary stream 4 flows as the secondary stream 5 along essentially the entire length of this treatment element through the membrane wall 3, collects in the cavity 2 which is open in the direction of the flow through the casing and leaves the treatment element at the lower end through opening 8.

Figure 6:
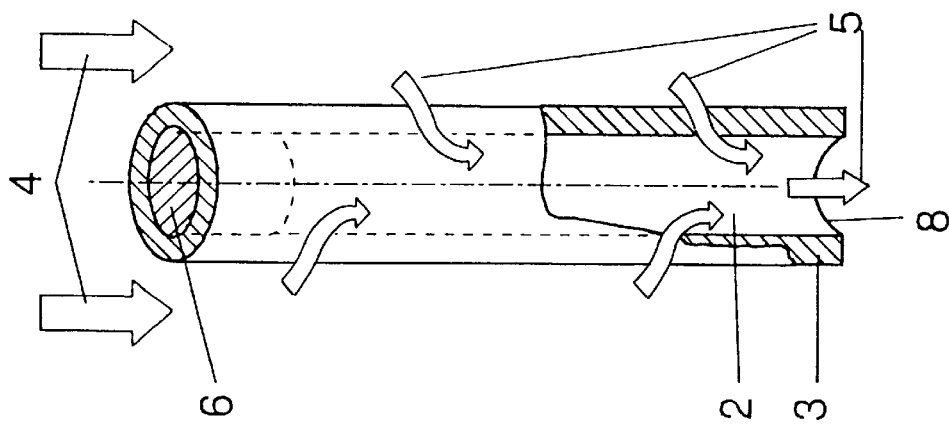
FIG. 6: Embodiment of a treatment element made from a hollow-fiber membrane with a cavity open on one side, produced by bending a hollow-fiber membrane section into a hairpin bend.

The treatment element shown in FIG. 6 is obtained by bending a hollow-fiber membrane section in the form of a hairpin bend and it has two openings 8 facing in the flow direction of primary stream 4 shown, and one continuous partially open cavity 2 with two halves corresponding to the halves of the treatment element. In the opposite direction to the flow direction of primary stream 4 shown, the cavity is closed. Instead of a hairpin bend shape, folding down the hollow-fiber membrane section is conceivable, by which means two separate cavities open on one side are formed.

The embodiment shown in FIG. 7 represents a treatment element with several partially open cavities 2 one behind the other. These cavities can be made by partially cutting into the hollow-fiber membrane at several points along its longitudinal axis, whereby at the points at which it is cut into, one cut edge 9 forms opening 8 of a cavity, and the other cut edge forms a stopper 10 of the adjacent end of the next cavity in line by means of gluing or welding it with the remaining wall of the hollow-fiber membrane. Here it is necessary to proceed in such a manner that all openings 8 of a treatment element of this kind face in the same direction and all closed ends of the cavities face in the opposite direction.

Figure 8:
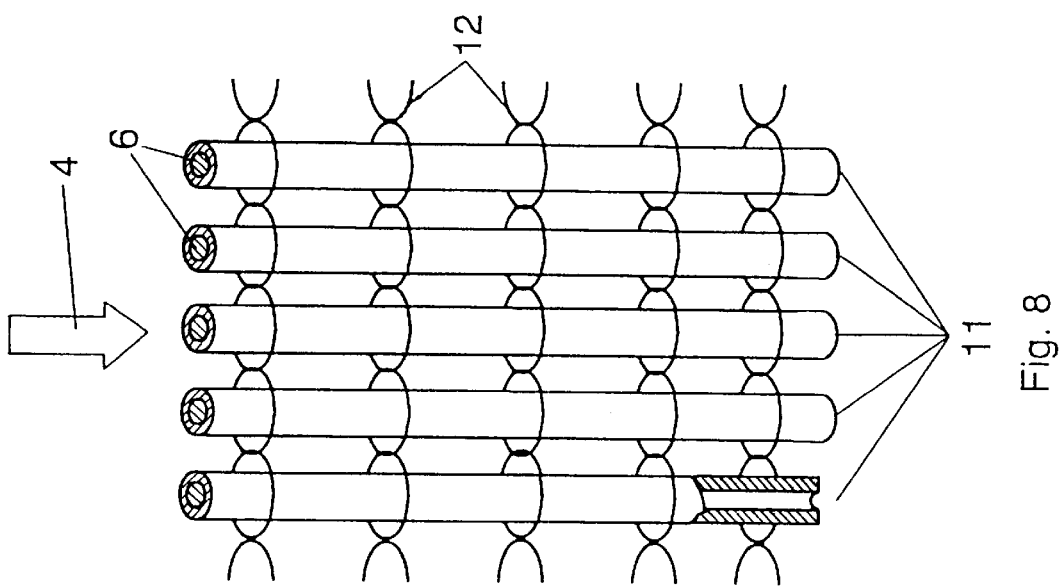
FIG. 8: Group of treatment elements made from hollow-fiber membranes with cavities open on one side, arranged side by side and bound in a mat.

FIG. 8 is a schematic representation of a group of treatment elements 11 arranged side by side made from hollow-fiber membranes with cavities open on one side bound into a mat by means of textile threads 12. A mat of this kind can be manufactured according to known processes, for example by means of weaving or knitting. The textile threads 12 hereby simultaneously take over the function of spacers and the hollow-fiber membrane treatment elements 11 are arranged essentially parallel to one another. In the example shown, the ends of the hollow-fiber membranes 11 facing the influx of the primary stream 4 are provided with stoppers 6. However, it can also be closed by means of welding the ends or by a bend between two adjacent hollow-fiber membrane elements as in FIG. 6.

Figure 9:
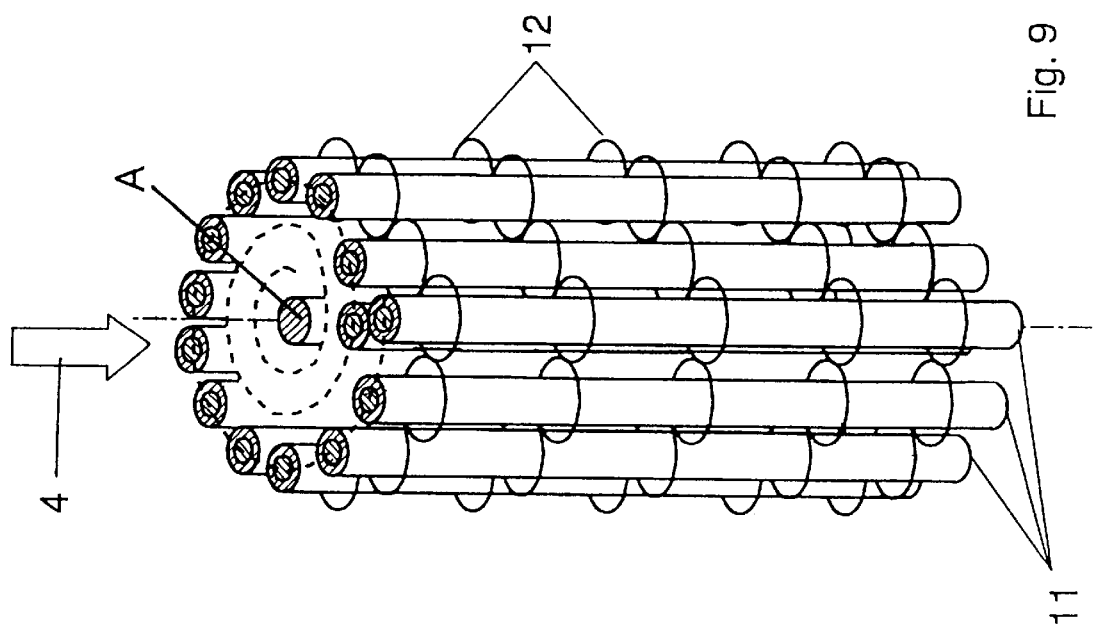
FIG. 9: Bundle made from a mat of treatment elements made from hollow-fiber membranes, the mat being spirally wound.

From a mat of this kind, a bundle-shaped group of treatment elements can be made by winding this mat in a spiral around an axis or a core, as shown schematically in FIG. 9. In this example, the mat is wound up in a spiral around a core A parallel to the hollow-fiber membranes, only the outer wound layer or lap being shown here. The continuation of the laps further in is represented by a spiral-shaped dashed line running through the axes of the hollow-fiber membranes arranged in the inside of the bundle. Here, the textile threads 12 linking the hollow-fiber membranes 11 keep apart both the hollow-fiber membranes lying next to each other in the mat and the hollow-fiber membranes lying next to each other in adjacent wound layers. With such a construction of groups of treatment elements, it is possible to achieve a high degree of order of the treatment elements and a high and uniform degree of filling of the device in accordance with the invention.

Figure 10:
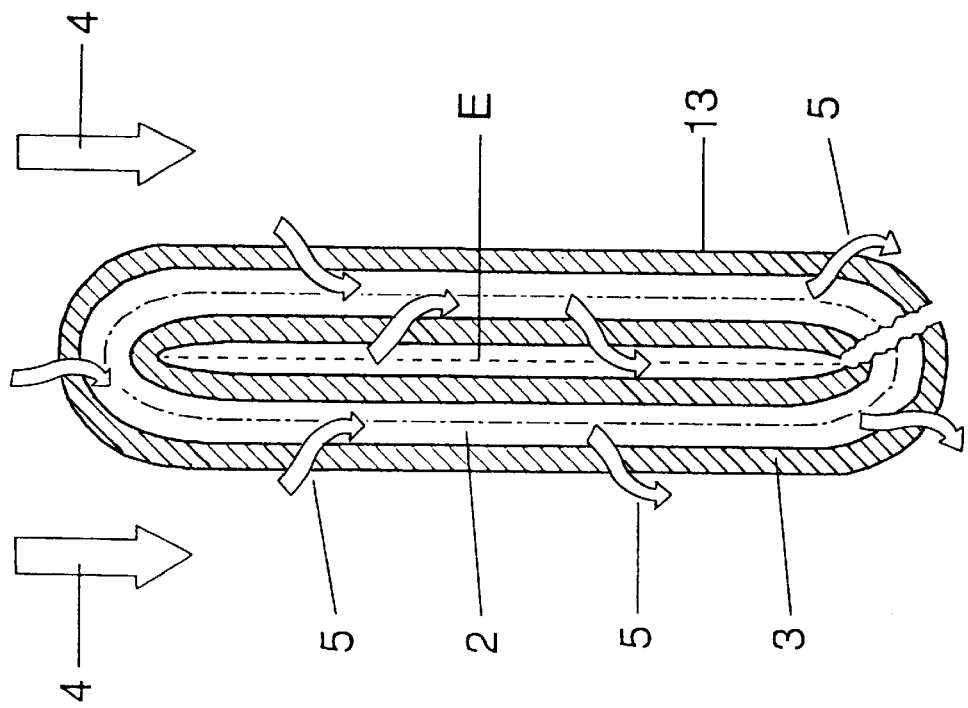
FIG. 10: Closed treatment element (segment) made from hollow-fiber membrane wound in a helix around a horizontal axis, cross-section.

In FIG. 10, a treatment element made from a hollow-fiber membrane is shown which has a closed cavity 2 and can be made in simple manner by winding a hollow-fiber membrane 13 in a helix around a horizontal axis or, as shown, around a plane E one extent of which is represented by a dashed line and whose longitudinal extent runs perpendicular to the plane of the figure. Only the section of the helix in the drawing plane is depicted schematically. Further turns adjoin the structure in the longitudinal direction perpendicular to the drawing plane. Here, it is preferable for there to be a spacing between the single turns of the helix so that in later use, a good flow around the hollow-fiber membranes forming the treatment element is guaranteed. The ends of the hollow-fiber membrane are closed, so that along the helix as a whole a continuous cavity 2 is formed which runs along the entire length of the hollow-fiber membrane. In the application, this helical treatment element is arranged in the casing such that the axis of the helix or the plane E around which this helix has been wound is arranged in its longitudinal extent perpendicularly to the direction of flow through the casing. By this means, the secondary stream flows in the part of the helix oriented in the opposite direction to the direction of the primary stream through the wall 3 of the hollow-fiber membrane into the cavity 2 of the treatment element and leaves the treatment element via the part oriented in the direction of the flow of the primary stream.

In a further step, a helical treatment element of this kind can be wound up in a spiral around an axis perpendicular to the axis of the helix or perpendicular to the longitudinal extent of the plane around which the helix is wound. This spirally wound treatment element can then be inserted into a casing, which expediently has a round cross-section, in such a manner that the axis of the spiral faces in the direction of the longitudinal axis of the casing.

Figure 11:
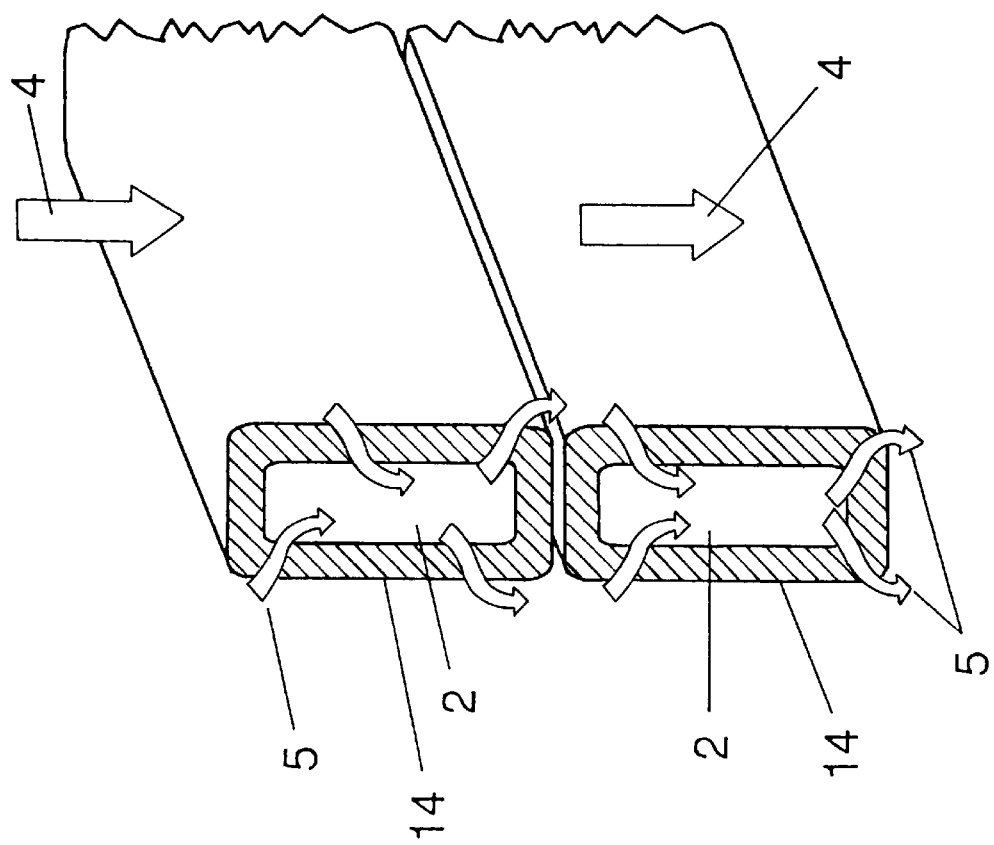
FIG. 11: Closed treatment element (segment) made from hollow-fiber membrane wound in a helix around a vertical axis, with flattened cross-section.

FIG. 11 shows a further embodiment of a treatment element made from a hollow-fiber membrane with a closed cavity. The structure of this treatment element is essentially similar to that shown in FIG. 10. Here, too, the hollow-fiber membrane is wound in a helix around an axis or around a plane which however runs parallel to the direction of the primary stream 4, whereby the ends of the hollow-fiber membrane forming the helix are closed. In the embodiment according to FIG. 11, a hollow-fiber membrane flattened in its cross-section is depicted as an example. In FIG. 11, sections of two adjacent laps 14 of the helix are shown, whereby the cavity cross-sections visible in the cross-sectional representation are cross-sections of the same cavity 2 due to the helical structure of the element.

In contrast to the treatment element according to FIG. 10, this treatment element is inserted into the casing of a device in accordance with the invention in such a manner that the axis of the helix, or the longitudinal extent of the plane around which the hollow-fiber membrane is wound in a helix, faces in the direction of the longitudinal axis of the casing and thus in the direction of the flow through the casing. By this means the primary stream 4 essentially flows perpendicularly towards the single turns of the helix. The secondary stream 5 penetrates through the part of the flattened hollow-fiber membrane which is oriented in the opposite direction to that of the primary stream, into the treatment element, collects in the cavity which runs along the entire length of the hollow-fiber membrane and leaves the treatment element on the side of the flattened hollow-fiber membrane oriented in the direction of flow of the primary stream 4. At the same time due to the total extent of the treatment element along its winding axis, a flow arises in the cavity of the treatment element in the direction of the longitudinal extent of the hollow-fiber membrane.

A treatment element of this kind can also be developed further, for example by arranging several layers of hollow-fiber membranes which are wound in a helix around an axis concentrically on top of one another, whereby the single layers are, for example, kept apart by means of suitable spacers in order to achieve good flow around the hollow-fiber membranes which form the single layers. Another option consists in winding at least one hollow-fiber membrane in several layers in a spiral on top of one another around an axis or around a core, whereby within a layer the at least one hollow-fiber membrane is wound in a helix around the axis or around the core.

Figure 12:
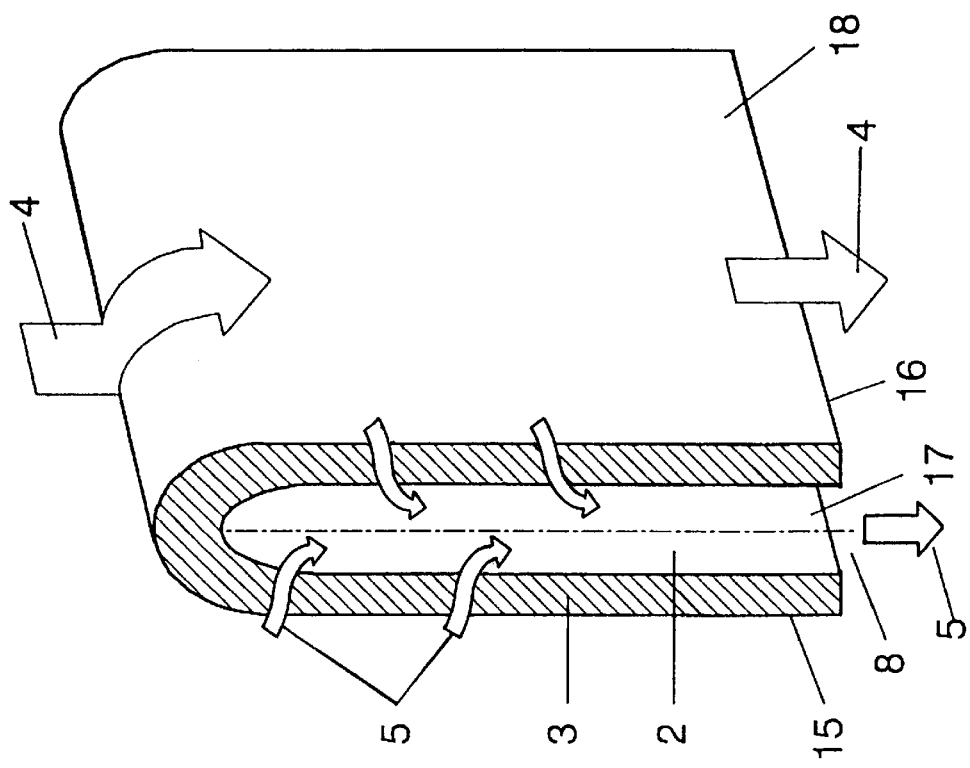
FIG. 12: Flat treatment element open on one side made from a flat membrane folded in a U-shape.

FIG. 12 shows a treatment element made from a flat membrane which is obtained, for example, by folding a rectangular section of a flat membrane in a U-shape. The two arms 15 and 16 of the folded flat membrane are kept apart from each other by a spacer—not shown here—for instance in the form of a liquid-permeable nonwoven. The cavity 2 of this treatment element is bounded by the arms of the flat membrane treatment element, the fold edge and the side edges joined together—not shown here—and has an opening 8 on the side opposite to the fold edge. The side of the flat membrane facing the cavity 2 represents the interior 17, while the other side of the flat membrane represents the exterior 18. In the application, the primary stream 4 flows around a treatment element of this kind, coming from the fold edge on its exterior. The secondary stream 5 enters from the exterior essentially along its entire extent into the membrane wall 3, collects in the cavity 2 of the treatment element and as a treated secondary stream leaves the treatment element at the open side 8 of the cavity in the direction of flow through the casing containing this treatment element.

Figure 13:
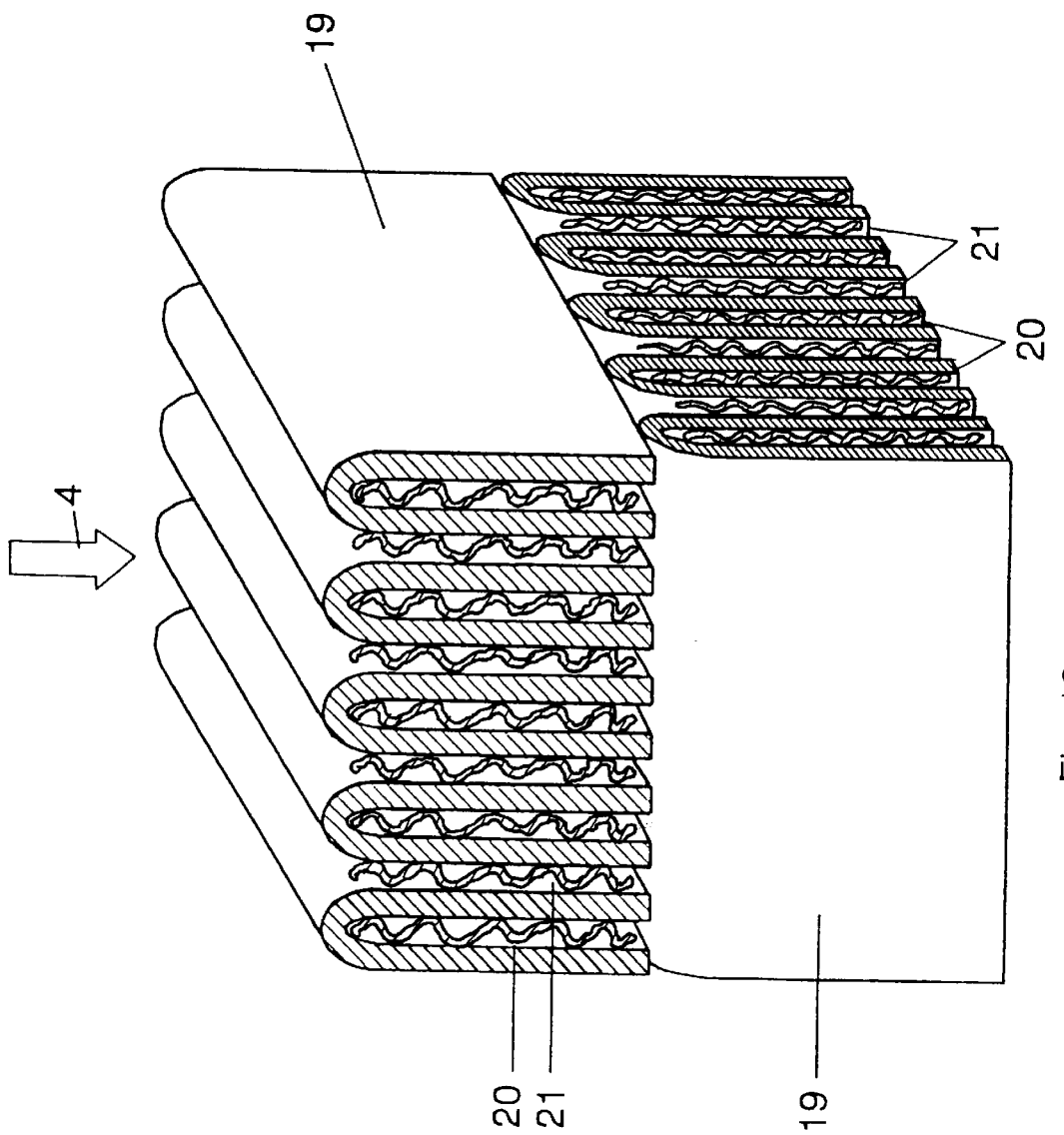
FIG. 13: Consecutive stages made from groups of flat membranes folded in a U-shape, rotated at an angle of 90° to each other.

FIG. 13 shows two consecutive stages 19 made from groups of plain flat-membrane treatment elements arranged in a stack side by side and folded in a U-shape. In this example, the fold edges of the treatment elements of adjacent stages are rotated 90° from each other. By this means, no spacer between the stages is necessary, whereby a good mixing of the primary stream and the secondary stream is still guaranteed. The treatment elements have fluid-permeable spacers 20 between the arms of which they comprise; the adjacent treatment elements within a stage are also kept apart by fluid-permeable spacers 21 in order thus to achieve a free flow by the primary stream 4 around the treatment elements on their exterior.

Figure 14:
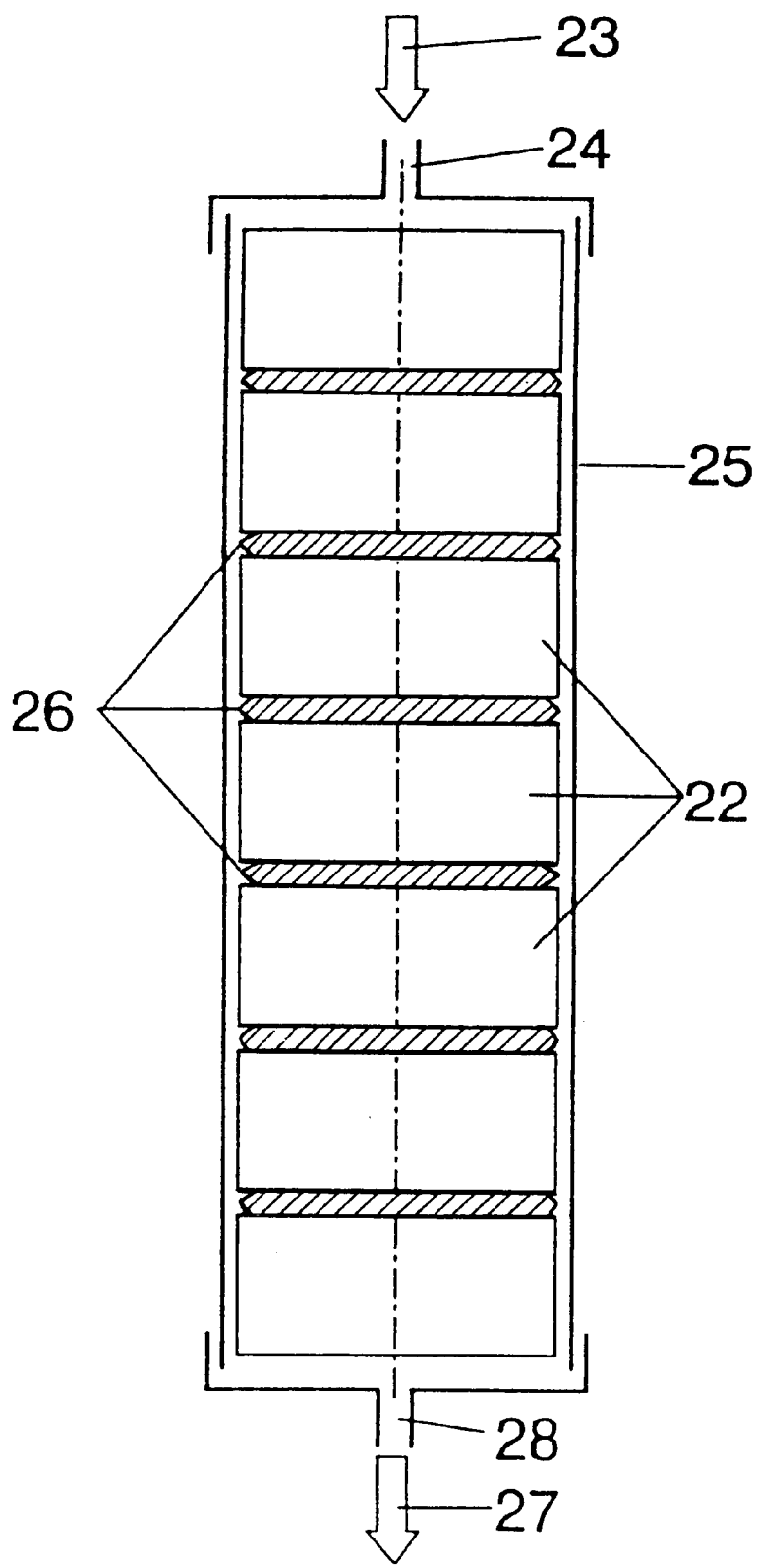
FIG. 14: Cross-section through a device in accordance with the invention.

In FIG. 14, a device containing multiple stages 22 of the treatment elements is depicted schematically in cross-section. The fluid to be treated enters the casing 25 of the device in accordance with the invention as the feed stream 23 through the inlet arrangement 24 and is uniformly distributed to the treatment elements of the first stage, possibly with the assistance of an appropriately designed distribution arrangement—not shown here. The fluid then runs consecutively through the stages 22 of treatment elements contained in the casing, in which the substance-specific treatment of the fluid takes place. Adjacent stages are kept apart in this example by the spacers 26 which are permeable to the fluid to be treated in order to enable the primary stream and the secondary stream to mix together well before the fluid to be treated enters the next stage. After running through the required number of stages 22, the treated fluid 27 is led out of the casing via the outlet arrangement 28.

What is claimed is:

1. Device for the substance-specific treatment of a fluid, comprising:

a casing, an inlet arrangement for introducing fluid to be treated into the casing, an outlet arrangement to remove the treated fluid from the casing, and at least one treatment element for the substance-specific treatment of the fluid with one end of the at least one treatment element facing the inlet arrangement and the other end facing the outlet arrangement, wherein the at least one treatment element has at least one cavity closed at least in the direction of the inlet arrangement and formed by one or more walls of the at least one treatment element, wherein the wall of the at least one treatment element is formed at least partially of at least one semi-permeable membrane with a porous structure, wherein the at least one treatment element is arranged in the casing such that between the inlet arrangement and the outlet arrangement, there is a continuous channel system located outside of and in contact with an exterior of the at least one treatment element and substantially surrounding the at least one treatment element at least at its end facing the inlet arrangement and at its end facing the outlet arrangement, and wherein the end facing the inlet arrangement and the end facing the outlet arrangement are free of any embedding surrounding the respective ends.

2. Device in accordance with claim 1, wherein at least one cavity has in the direction of the outlet arrangement an opening which leads into the channel system.

3. Device in accordance with claim 1, wherein the at least one cavity has a ratio L/D of cavity dimension L in the direction of the extent of the channel system between the inlet arrangement and the outlet arrangement and the hydraulic diameter D of the cavity cross-section perpendicular to the cavity of between 2 and 4000.

4. Device in accordance with claim 1, wherein the at least one treatment element has a ratio $V_w/V_t$ of the volume of the treatment element walls $V_w$ to the volume of the treatment element $V_t$ comprising the volume of the walls $V_w$ and the volume of the at least one cavity $V_c$ between 0.5 and 0.98.

5. Device in accordance with claim 1, wherein the walls of each treatment element have a substantially uniform thickness.

6. Device in accordance with claim 1, wherein the device has at least one group of several treatment elements, which treatment elements are arranged side by side substantially transverse to the direction of the extent of the channel system between the inlet arrangement and the outlet arrangement.

7. Device in accordance with claim 6, wherein the treatment elements put together into at least one group are spaced apart from one another by spacers.

8. Device in accordance with claim 7, wherein the treatment elements arranged in the casing and adjacent to an inner wall of the casing are at a distance from the inner wall of the casing which is smaller than or equal to the distance between the treatment elements.

9. Device in accordance with claim 1, wherein several treatment elements or groups of treatment elements are arranged as stages one behind the other in the casing in the direction of the extent of the channel system between the inlet arrangement and the outlet arrangement.

10. Device in accordance with claim 1, wherein a ratio $V_T/V_C$ of a total volume $V_T$ of all treatment elements comprising the sum of volumes $V_t$ of the single treatment elements and volume $V_C$ of the empty casing is between 0.4 and 0.95.

11. Device in accordance with claim 10, wherein the ratio is between 0.55 and 0.75.

12. Device in accordance with claim 1, wherein the membrane has an average pore diameter between 0.005 $\mu$m and 5 $\mu$m.

13. Device in accordance with claim 12, wherein the membrane has an average pore diameter between 0.1 $\mu$m and 3 $\mu$m.

14. Device in accordance with claim 1, wherein the membrane has a substantially constant average pore diameter along at least 80% of the extent of the membrane in the direction of the extent between the channel system and the at least one cavity.

15. Device in accordance with claim 14, wherein the membrane has a layer on a side facing the channel system which has a smaller average pore diameter than an adjacent region of the membrane in the direction of the at least one cavity.

16. Device in accordance with claim 15, wherein the layer is between 1 $\mu$m and 5 $\mu$m thick.

17. Device in accordance with claim 15, wherein the average pore diameter in the layer is smaller by a factor of 5 to 50 than that in the adjacent region.

18. Device in accordance with claim 1, wherein the membrane has an average porosity between 50 and 90% by volume.

19. Device in accordance with claim 1, wherein the membrane has a BET surface between 2 and 300 m$^2$ per cm$^3$ membrane volume.

20. Device in accordance with claim 19, wherein the membrane has a BET surface between 4 and 30 m$^2$ per cm$^3$ membrane volume.

21. Device in accordance with claim 1, wherein the membrane is a hollow-fiber membrane and the wall of the hollow-fiber membrane is the wall of the at least one cavity, and the hollow-fiber membrane is closed at least at one end.

22. Device in accordance with claim 21, wherein a group of treatment elements lying side by side have a plurality of hollow-fiber membranes spaced apart with textile threads.

23. Device in accordance with claim 22, wherein the hollow-fiber membranes of a group are bound into at least one hollow-fiber mat by means of the textile threads.

24. Device in accordance with claim 23, wherein the at least one hollow-fiber mat is selected from the group consisting of a woven mat, a knitted mat and a woven tape.

25. Device in accordance with claim 23, wherein the at least one hollow-fiber mat is spirally wound up around an axis parallel to the direction of the extent of the channel system between the inlet arrangement and the outlet arrangement.

26. Device in accordance with claim 23, wherein at least two hollow-fiber mats are laid on top of each other and spirally wound up around an axis parallel to the direction of the extent of the channel system between the inlet arrangement and the outlet arrangement and the hollow-fiber mats are laid on top of each other such that the hollow fibers of the hollow-fiber mats laid on top of each other are brought into a criss-cross arrangement.

27. Device in accordance with claim 1, wherein the at least one treatment element is formed from at least one flat membrane.

28. Device in accordance with claim 27, wherein the at least one treatment element is formed from a flat membrane folded in a U-shape, whereby the fold edge formed by folding is arranged in the direction of the inlet arrangement and whereby arms of the flat membrane folded in a U-shape thus produced are kept apart in order to form the at least one cavity.

29. Device in accordance with claim 27, wherein the at least one treatment element is formed from two flat membranes parallel to each other and kept apart from each other, whereby the two flat membranes are joined together positively at least at edges facing in the direction of the inlet arrangement.

30. Device in accordance with claim 27, wherein the at least one flat membrane is spirally wound around an axis parallel to the direction of the extent of the at least one flat membrane between the inlet arrangement and the outlet arrangement such that a closed edge faces in the direction of the inlet arrangement, whereby laps of the wound membranes are spaced apart by spacers and channels are formed between the laps, which are part of the channel system.

31. Device in accordance with claim 1, wherein the membrane comprises polytetrafluoroethylene, polyvinylidene fluoride or modifications, blends, mixtures or copolymers thereof.

32. Device in accordance with claim 1, wherein groups with a substance-specific action are immobilized on and/or in the membrane.

33. Device in accordance with claim 32, wherein the groups with a substance-specific action are ligands for affinic separation of ligates from the liquid to be treated.

34. Device in accordance with claim 33, wherein the ligands are coupled to the membrane via molecules of long-chain linear polymers, whereby the molecules of the long-chain linear polymers carry a plurality of ligands.

35. Device in accordance with claim 32, wherein the groups with a substance-specific action are enzymes.

36. Device in accordance with claim 32, wherein the groups with a substance-specific action are catalysts.

37. Process for the substance-specific treatment of a fluid, comprising sending the fluid through the device according to claim 1.

38. Process for the substance-specific treatment of a fluid using a semi-permeable membrane with a porous structure arranged in the casing, wherein the membrane has at least a first surface defining its exterior and at least a second surface defining its interior, comprising:

feeding the fluid to be treated into the casing, causing the fluid to flow through the casing, whereby the fluid is caused to flow along the exterior of the membrane as a primary stream but not along the interior, and a part of the primary stream flows as a secondary stream into the membrane via the exterior and through the membrane, where the substance-specific treatment of the fluid takes place with the secondary stream, wherein a remaining portion of the primary stream flows substantially freely around an entire extent of the exterior of the membrane and wherein the secondary stream is fed back, within the casing and after the substance-specific treatment, to the remaining portion of the primary stream flowing at the exterior of the membrane to form a combined stream, and removing the combined stream from the casing.

39. Process in accordance with claim 38, wherein the fluid to be treated is a suspension.

40. Process in accordance with claim 38, wherein the membrane is selected from the group consisting of a hollow-fiber membrane and a flat membrane.

41. Process in accordance with claim 38, wherein the membrane is formed into at least one treatment element that has at least one cavity closed at least in the direction opposite to the direction of the flow through the casing.

42. Process in accordance with claim 41, wherein at least one cavity has an opening which faces in the direction of the flow through the casing.

43. Process in accordance with claim 41, wherein the membrane has at least one group of several treatment elements, which treatment elements are arranged side by side substantially transverse to the direction of flow through the casing.

44. Process in accordance with claim 41, wherein the treatment of the fluid is conducted in several treatment elements or groups of treatment elements as stages spatially arranged one behind the other in the direction of the flow through the casing.

45. Process in accordance with claim 44, wherein the number of stages is between 1 and 1000.

46. Process in accordance with claim 44, wherein the number of stages is between 2 and 100.

47. Process in accordance with claim 44, wherein between the individual stages, the fluid is mixed.

48. Process in accordance with claim 38, wherein several casings with treatment elements arranged in them are arranged one behind the other.

49. Process in accordance with claim 38, wherein the fluid to be treated is recirculated.

50. Process in accordance with claim 38, wherein the process is carried out with a device for the substance-specific treatment of a fluid in which the device comprises:

a casing, an inlet arrangement for introducing the fluid to be treated into the casing, an outlet arrangement to remove the treated fluid from the casing, and at least one treatment element for the substance-specific treatment of the fluid with one end of the at least one treatment element facing the inlet arrangement and the other end facing the outlet arrangement, wherein the at least one treatment element has at least one cavity closed at least in the direction of the inlet arrangement and formed by one or more walls of the at least one treatment element, wherein the wall of the at least one treatment element is formed at least partially of at least one semipermeable membrane with a porous structure, and wherein the at least one treatment element is arranged in the casing such that between the inlet arrangement and the outlet arrangement, there is a continuous channel system located outside of and in contact with an exterior of the at least one treatment element and substantially surrounding the at least one treatment element at least at its end facing the inlet arrangement and at its end facing the outlet arrangement, and wherein the end facing the inlet arrangement and the end facing the outlet arrangement are free of any embedding surrounding the respective ends.

51. Process in accordance with claim 38, wherein the process is for the purification or separation of ligates from a liquid containing ligates by means of affinity chromatography, wherein the membrane has immobilized thereon and/or therein ligands for the aforementioned ligates.

52. Process in accordance with claim 38, wherein the process is for the enzymatic treatment of a liquid, wherein the membrane has immobilized thereon and/or therein enzymes.

53. Process in accordance with claim 38, wherein the process is for the catalytic treatment of a fluid, wherein the membrane has immobilized thereon and/or therein catalysts.

54. Device according to claim 1, wherein the continuous channel system is maintained by one or more of spacers, the shape of the at least one treatment element or the shape of the inner wall of the casing.

55. Device according to claim 54, wherein the at least one treatment element is a single treatment element, and wherein the continuous channel system is located between an inner wall of the casing and the exterior of the single treatment element.

56. Device according to claim 54, wherein the at least one treatment element comprises a group of individual treatment elements, and wherein the continuous channel system is located between the individual treatment elements and between an inner wall of the casing and the exterior of outer individual treatment elements.

* * * * *

UNITED STATES PATENT AND TRADEMARK OFFICE
CERTIFICATE OF CORRECTION

PATENT NO. : 6,022,478
DATED : February 8, 2000
INVENTOR(S) : Ulrich Baurmeister and Rudolf Wollbeck It is certified that error appears in the above-identified patent and that said Letters Patent is hereby corrected as shown below:

Title page,
Iem [56] References Cited, please add the following:

U.S. PATENT DOCUMENTS 4,940,617      7/1990      BAURMEISTER

FOREIGN PATENT DOCUMENTS

WO 92/18609   10/1992    WIPO
WO 91/10492   7/1991     WIPO

Signed and Sealed this

Thirtieth Day of October, 2001

Attest:

NICHOLAS P. GODICI
Attesting Officer    Acting Director of the United States Patent and Trademark Office